(12) United States Patent
Hashimotodani et al.

(10) Patent No.: US 8,702,930 B2
(45) Date of Patent: Apr. 22, 2014

(54) SENSOR CHIP AND STORAGE METHOD THEREOF

(75) Inventors: Kiyoshi Hashimotodani, Kyoto (JP); Yusuke Nakano, Osaka (JP); Masaya Nakatani, Hyogo (JP); Takeki Yamamoto, Hyogo (JP); Yoshiki Yamada, Osaka (JP); Takuya Oka, Kyoto (JP); Hiroshi Ushio, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/636,976

(22) PCT Filed: Jan. 11, 2012

(86) PCT No.: PCT/JP2012/000105
§ 371 (c)(1), (2), (4) Date: Sep. 24, 2012

(87) PCT Pub. No.: WO2012/096162
PCT Pub. Date: Jul. 19, 2012

(65) Prior Publication Data
US 2013/0008786 A1      Jan. 10, 2013

(30) Foreign Application Priority Data

Jan. 13, 2011  (JP) .................................. 2011-004691
Jul. 25, 2011  (JP) .................................. 2011-161669
Jul. 25, 2011  (JP) .................................. 2011-161670
Jul. 25, 2011  (JP) .................................. 2011-161675
Jul. 25, 2011  (JP) .................................. 2011-161676

(51) Int. Cl.
*G01N 33/487*   (2006.01)
*G01N 27/28*    (2006.01)

(52) U.S. Cl.
USPC ..... 204/403.01; 977/924; 204/400; 422/68.1; 422/82.01; 435/287.1; 435/287.2; 428/447; 427/387; 600/364

(58) Field of Classification Search
USPC ......... 204/403.01–403.15; 600/364; 428/447; 427/387; 205/775, 777.5, 792, 793, 205/781, 778; 422/68.1, 82.01; 435/287.1, 435/287.2
See application file for complete search history.

(56) References Cited

U.S. PATENT DOCUMENTS 6,863,833 B1   3/2005  Bloom et al.
6,936,462 B1   8/2005  Owen et al.
(Continued)

FOREIGN PATENT DOCUMENTS

JP   2002-518678 A    6/2002
JP   2010-213668 A    9/2010
(Continued)

OTHER PUBLICATIONS

Mizokuro et al. (J. Appl. Phys., vol. 85, No. 5, Mar. 1, 1999).*

(Continued)

*Primary Examiner* — Jennifer Dieterle
(74) *Attorney, Agent, or Firm* — McDermott Will & Emery LLP

(57) ABSTRACT

A sensor chip is a sensor device for measuring a property of a substance by adsorbing the substance on a surface of the sensor chip. The sensor chip includes a diaphragm having a first surface, a second surface, and at least one through hole penetrating from the first surface to the second surface. At least a part of the first surface, the second surface, and an inner wall surface of the through hole is covered with a noncrystalline solid layer including SiOX as a main component, in which substance X is an element having higher electronegativity than that of silicon.

10 Claims, 20 Drawing Sheets

(56) References Cited

U.S. PATENT DOCUMENTS

| | | | |
|---|---|---|---|
| 7,723,029 B2 | 5/2010 | Huang et al. | |
| 2005/0102721 A1* | 5/2005 | Barth | 977/DIG. 001 |
| 2005/0221282 A1 | 10/2005 | Owen et al. | |
| 2005/0266478 A1 | 12/2005 | Huang et al. | |
| 2006/0251544 A1 | 11/2006 | Taboryski et al. | |
| 2009/0153153 A1* | 6/2009 | Vogel et al. | 324/692 |
| 2011/0048939 A1 | 3/2011 | Owen et al. | |
| 2011/0120864 A1* | 5/2011 | Takahashi et al. | 204/403.01 |

FOREIGN PATENT DOCUMENTS

| WO | WO-2003/093494 A2 | | 11/2003 |
|---|---|---|---|
| WO | WO2010/016193 | * | 2/2010 |

OTHER PUBLICATIONS

Murakawa et al. (Japanese Journal of Applied Physics 49, 2010).*
International Search Report issued in International Application No. PCT/JP2012/000105 issued on Apr. 17, 2012.
Coronado., "Effect of divalent cations on the assembly of neutral and charged phospholipid bilayers in patch-recording pipettes", Biophysical Journal, vol. 47, Issue 6 , 851-857, Jun. 1, 1985.
Lee et al., "Preparation of glass capillary columns for gas chromatography", Journal of Chromatography, vol. 184, (1980), pp. 235-312.
Itoh et al., "A novel method for glass micropipette polishing for electropatch clamp recording using oxygen plasma", Biochem Biophys Res Commun. Mar. 15, 1993;191(2):447-52.

* cited by examiner

SENSOR CHIP AND STORAGE METHOD THEREOF

RELATED APPLICATIONS

This application is the U.S. National Phase under 35 U.S.C. §371 of International Application No. PCT/JP2012/000105, filed on Jan. 11, 2012, which in turn claims the benefit of Japanese Application Nos. 2011-004691, filed on Jan. 13, 2011, 2011-161675, filed on Jul. 25, 2011, 2011-161676, filed on Jul. 25, 2011, 2011-161669, filed on Jul. 25, 2011 and 2011-161670, filed on Jul. 25, 2011, the disclosures of which Applications are incorporated by reference herein.

TECHNICAL FIELD

The present invention relates to a sensor chip used for, for example, a biosensor and a chemical substance identification sensor for measuring a property of a substance by adsorbing the substance on a surface thereof, and relates to a storage method of the sensor chip.

BACKGROUND ART

A conventional cell electrophysiological measurement device as an example of a sensor device can allow a cell as a biomaterial substance to be adsorbed on a surface of a sensor chip and measure the property of the cell. The patch-clamp method in electrophysiology is known as a method for measuring an ion channel that is present in a cell membrane. The patch-clamp method has elucidated various functions of the ion channel. The functions of the ion channel are important interest in the cytology, and are applied for developing agents.

On the other hand, however, the patch-clamp method requires an operation based on extremely advanced technique of inserting a minute micropipette into a single cell with high accuracy. Therefore, even a skilled operator cannot carry out much measurement. Therefore, the patch-clamp method is not so suitable when measurement with high throughput is required.

Thus, flat-shaped cell electrophysiological measurement devices using a fine processing technique have been developed. These devices are suitable for an automated patch system that does not require insertion of a micropipette into individual cells.

A cell electrophysiological measurement device includes, for example, a mount board made of resin, and a sensor chip inserted into a communicating hole provided on a bottom surface of the mount board. The sensor chip is made of silicon or glass. Furthermore, the sensor chip includes a curved or flat surface partition plate provided with at least one or more through holes. The opening diameter of the through hole is 1 micrometer to 3 micrometers. The cell electrophysiological measurement device includes a single-hole sensor chip having one through hole in one sensor chip, and a multi-hole sensor chip having a plurality of through holes in one sensor chip.

An upper electrolytic chamber disposed on the upper side of the partition plate of the mount board and a lower electrolytic chamber disposed on the lower side of the partition plate of the mount board are filled with an electrolytic solution. The upper electrolytic chamber and the lower electrolytic chamber are divided by the partition plate included in the mount board and the sensor chip.

Then, a cell as a specimen is injected from the upper electrolytic chamber, the cell is adsorbed on an opening at the upper electrolytic chamber side of the through hole by pressurizing from the upper electrolytic chamber or sucking from the lower electrolytic chamber. The opening diameter of the through hole is 1 micrometer to 3 micrometers. This range is suitable for holding and adsorbing a cell. A part of a sucked cell membrane is extended to the inside of the through hole and fixedly attached to a wall surface of the through hole.

In this state, for example, an agent is administered to the periphery of the cell, and potential difference or an electric current generated between the upper and lower electrolytic chambers is measured by using electrodes each of which is disposed inside the upper and lower electrolytic chambers, and thereby a pharmacological reaction of the cell with respect to the administered agent can be determined (PTL 1).

It is more difficult to establish a high-resistance seal between the sensor chip and a cell in a conventional flat-shaped cell electrophysiological measurement device as compared with the patch-clamp method using a glass pipette. Herein, a high-resistance state in which the sensor chip and a cell are fixedly attached to each other strongly is referred to as a gigaseal state.

Furthermore, a plane (a cell contact plane) which a cell is brought into contact with and fixedly attached to is a partition plate and a wall surface of a through hole. In order to increase the degree of adhesion of a cell and to form strong fixedly-attached state, a silanol group (SiOH group) is required to be sufficiently formed on the surface of the cell contact plane. An exemplary embodiment in which the degree of adhesion between a cell contact plane of a glass pipette and a cell is increased is disclosed (NPTL 1). Furthermore, there is also a disclosure that surface energy and a hydrophilic property are changed depending upon the amount of silanol groups attached on the surface of glass or $SiO_2$ (NPTL 2). That is to say, in order to fixedly attach a cell to the cell contact plane strongly, a sufficient amount of silanol groups is required to be attached. The amount of silanol groups can be indirectly evaluated by the hydrophilic property of the surface, a surface charge, or the like.

Examples of methods for improving the hydrophilic property of the surface of glass or $SiO_2$ include a method using plasma such as oxygen plasma and atmospheric plasma, a method of irradiation with light with high energy, for example, excimer UV right exposure, a method of washing with a mixture solution of sulfuric acid and a hydrogen peroxide solution, and the like. In this way, methods commonly used in production of semiconductors or production of MEMS devices can be employed (NPTL 3).

Furthermore, in order to form a gigaseal state, a method for enhancing an activity by subjecting a silicon dioxide layer on the surface of the chip surface to treatment with, for example, oxygen plasma may be employed. For example, there is a disclosure that a chip surface is subjected to acid/base treatment, oxygen plasma treatment, or the like, thereby forming SiOM (M represents H or metal such as Na, K, Mg, and Ca) (NPTL 2).

Alternatively, film formation of a silicon nitride layer containing $Si_3N_4$ as a main component on a surface of a chip by using a LPCVD (Low Pressure Chemical Vapor Diposition) method is disclosed (PTLs 3 and 4).

In conventional sensor devices, when measurement is carried out in a short time after a sensor device is produced, measurement can be carried out with an amount of silanol groups formed on the surface kept sufficient. However, when it is necessary to store a large number of sensor devices produced simultaneously for a considerable time before measurement is started, it is necessary to store the sensor devices while the silanol groups formed on the surface are kept in a sufficient amount. In a conventional sensor device, for example, in a storage state before measurement is carried out by inputting a cell, a silanol group on the surface of the sensor device is dissociated so as to form Si.O.Si (a siloxane bond). Alternatively, a substance that inhibits adsorption of a cell to be measured (hereinafter, referred to as an "adsorption inhibiting substance") is adsorbed on the surface of the sensor device, which may make attachment of the cell insufficient and reduce the accuracy of measurement.

That is to say, in a conventional cell electrophysiological measurement device as one example of a sensor device, a cell is not sufficiently adsorbed on the through hole because a cell adsorption inhibiting substance is present on a surface of a through hole on which the cell formed on a sensor chip is to be adsorbed. Therefore, a leakage current may be generated between the cell surface and the through hole surface, so that it is difficult to improve the measurement accuracy. Therefore, as means for preventing of silanol groups from being dissociated and means for preventing adsorption inhibiting substances from being adsorbed on the surface of through hole, underwater storage for storing a sensor device in water, vacuum storage for storing a sensor device in a vacuum chamber, and inert gas storage for storing a sensor device in an atmosphere of an inert gas such as $N_2$, immediately before a cell is measured. However, the underwater storage requires work for pulling water out of the sensor before measurement, and the vacuum storage or the inert gas storage may be insufficient in terms of a storage effect.

In particular, the dissociation of silanol groups advances a mechanism for forming $H_2O$ in which, as shown in the chemical formula Chem. 1, two silanol groups adjacent to each other on the surface are dissociated and bound. Therefore, the vacuum storage or the inert gas storage may have an effect for preventing attachment of adsorption inhibiting substances, dissociation of silanol groups and generation of $H_2O$ cannot be prevented. Therefore, in the vacuum storage and the inert gas storage, an effect for preventing deterioration of the hydrophilic property is limited.

 [Chem. 1]

Note here that examples of prior art mentioned above include the following patent literatures and non-patent literatures.

CITATION LIST

Patent Literatures

PTL 1: Japanese Translation of PCT Publication No. 2002-518678
PTL 2: U.S. Pat. No. 7,723,029
PTL 3: U.S. Pat No. 6,863,833
PTL 4: US Patent Application Publication No. 2006/0251544

Non-Patent Literatures

NPTL 1: Effect of Divalent Cations on The assemble of neutral and charged phospholipid bilayers in patch-recording pipettes, Roberto Coronado, Biophysics J. Volume 47, June 1985.
NPTL 2: Preparation of glass capillary columns for GAS CHROMATOGRAPHY, Milton L. LEE and BOB W. Wright, Journal of Chromatography, 184(1980) 235-312
NPTL 3: Biochemical and biophysical research communications, Vol. 191 No.2 P. 447 (1993)

SUMMARY OF THE INVENTION

A sensor chip of the present invention is a sensor chip for measuring a property of a substance by adsorbing the substance on a surface of the sensor chip. The sensor chip includes a diaphragm including a first surface, a second surface, and at least one through hole penetrating from the first surface to the second surface. At least a part of the first surface, the second surface, and an inner wall surface of the through hole is covered with a noncrystalline solid layer including SiOX as a main component, in which substance X is an element having higher electronegativity than that of silicon.

DETAILED DESCRIPTION OF THE PREFERRED EMBODIMENT

First Exemplary Embodiment

Figure 1:
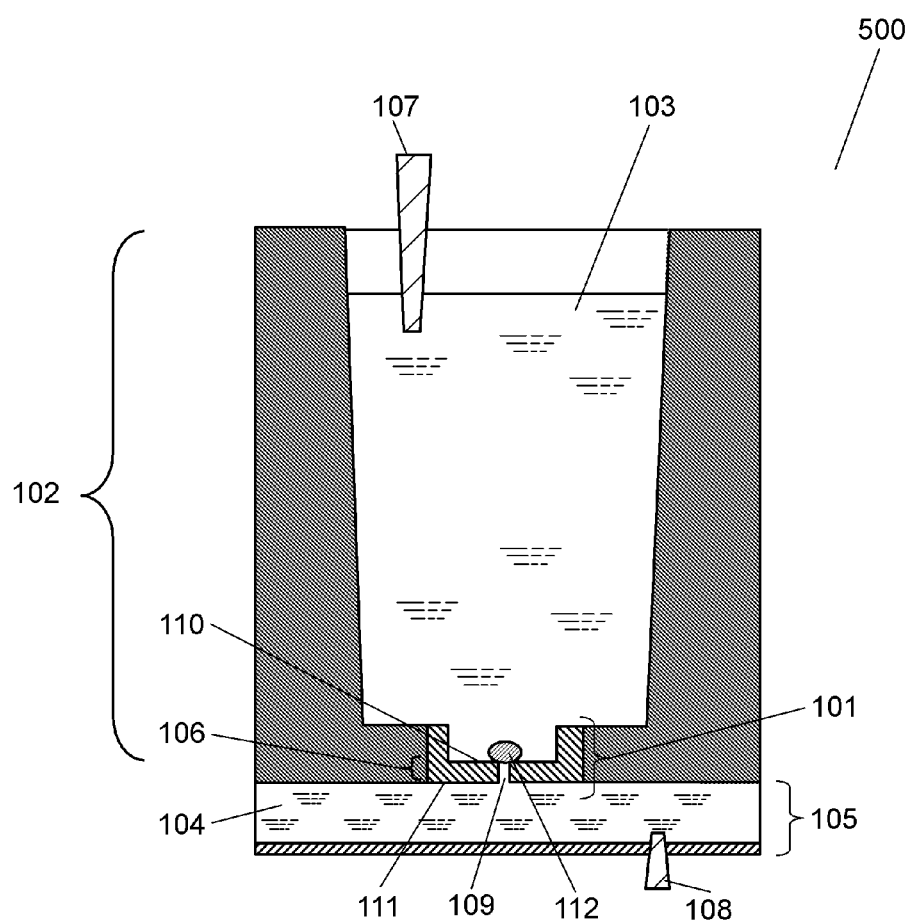
FIG. 1 is a sectional view of a sensor device in accordance with an exemplary embodiment of the present invention.

FIG. 1 is a sectional view of a sensor device in accordance with an exemplary embodiment of the present invention. Hereinafter, sensor device 500 is described with reference to drawings. This exemplary embodiment describes an example in which sensor chip 101 is used for a cell electrophysiological measurement device.

Furthermore, sensor device 500 using a single-hole sensor chip having one through hole 109 in one sensor chip 101 is described.

Sensor chip 101 is fixed on a bottom surface of well 102. Well 102 is a well-type container obtained by molding resin materials such as polystyrene and polycarbonate. Specimen 112 as a biological sample material such as a cell to be measured is held in first electrolytic solution 103 in well 102.

Furthermore, flow passage 105 is provided below well 102. Flow passage 105 is filled with second electrolytic solution 104. First electrolytic solution 103 and second electrolytic solution 104 are separated from each other by diaphragm 106 corresponding to a bottom part of sensor chip 101. First electrode 107 is disposed in contact with first electrolytic solution 103 in well 102. Second electrode 108 is disposed in contact with second electrolytic solution 104 in flow passage 105. Second electrode 108 is not necessarily required to be formed in flow passage 105, and it is only required to be disposed such that it is brought into contact with second electrolytic solution 104.

Specimen 112 in a solution filled in well 102 is sucked and held on through hole 109 by applying a negative pressure from flow passage 105 side via through hole 109 provided in diaphragm 106, or applying a positive pressure from well 102 side. At this time, the inner periphery of through hole 109 and specimen 112 are strongly brought into contact with each other so as to form a seal.

In measurement, a small pore is formed in specimen 112 inside through hole 109 by sucking specimen 112 more strongly from flow passage 105 side via through hole 109, or introducing a specific agent (for example, nystatin) in second electrolytic solution 104 in flow passage 105. This is generally called a perforated patch technique. With this pore, first electrolytic solution 103 and second electrolytic solution 104 communicate with each other via specimen 112.

Thereafter, an operation as stimulation is carried out with respect to specimen 112 from well 102 side. Examples of the operation include physical stimulation by, for example, mechanical displacement such as electromagnetic wave and vibration, light, and heat, in addition to chemical stimulation with, for example, chemical agents or toxic agents.

When specimen 112 actively responds to such stimulation, an ion channel existing in the cell membrane of specimen 112 is opened and closed. Thereby, an ionic current is generated between first electrolytic solution 103 and second electrolytic solution 104 via specimen 112. An electric change occurring with the ionic current is detected by first electrode 107 and second electrode 108. At this time, when the seal between the inner periphery of through hole 109 and specimen 112 is imperfect, leakage of an electric current flowing via such an imperfect seal not via specimen 112 occurs, thus making it difficult to measure the ionic current by ionic channel response. Therefore, a sealing property between through hole 109 and specimen 112 is extremely important. When the seal is ideal, an electrical resistance value (seal resistance value) between first electrode 107 and second electrode 108 exhibits an extremely high value exceeding $10^9 \Omega$. Such a state is referred to as gigaseal.

Figure 2A:
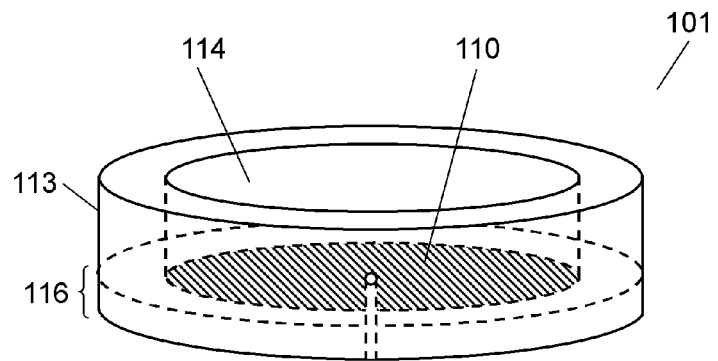
FIG. 2A is a perspective view of a single-hole sensor chip in accordance with the exemplary embodiment of the present invention.
Figure 2B:
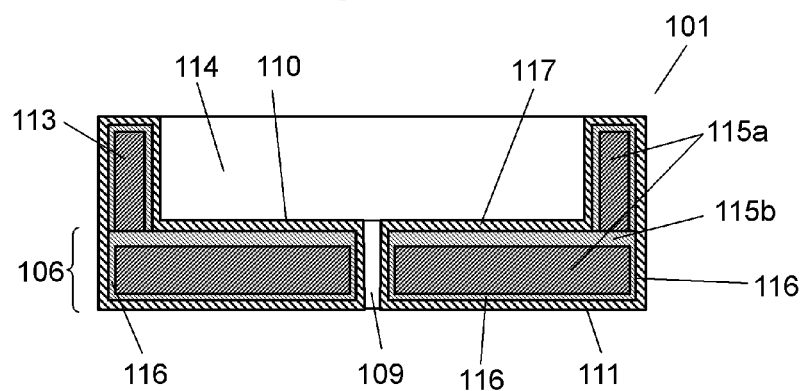
FIG. 2B is a sectional view of the single-hole sensor chip in accordance with the exemplary embodiment of the present invention.

FIG. 2A is a perspective view of a single-hole sensor chip in accordance with this exemplary embodiment. FIG. 2B is a sectional view of a single-hole sensor chip in accordance with this exemplary embodiment.

Sensor chip 101 is a circular cylinder having a diameter of about 1 mm, and has cylindrical concave portion 114 having a diameter of 600 μm in the center part thereof. The outer periphery of concave portion 114 is surrounded by wall layer 113. As shown in FIG. 2B, diaphragm 106 corresponding to a bottom part of concave portion 114 has first surface 110 and second surface 111. First surface 110 is brought into contact with first electrolytic solution 103 at well 102 side. Second surface 111 is provided at the opposite side to first surface 110, and is brought into contact with second electrolytic solution 104 at flow passage 105 side. First surface 110 and second surface 111 are connected to each other with through hole 109. Note here that a sensor chip structure described herein is just an example, and sizes and numeric values are not necessarily limited to this example.

At least a part of surfaces of first surface 110 and second surface 111 of diaphragm 106 is covered with noncrystalline solid layer 117 containing SiOX as a main component. Furthermore, a surface on which specimen 112 is captured is covered with noncrystalline solid layer 117. Herein, substance X is a substance whose electronegativity is higher than that of silicon as mentioned below.

The diameter of through hole 109 is desirably not less than 1 μm and not more than 10 μm, and further desirably not less than 1.7 μm and not more than 2.3 μm. When the diameter of through hole 109 is less than 1 μm, it becomes difficult to maintain the gigaseal for a long time. Furthermore, second electrolytic solution 104 cannot easily reach specimen 112, and accordingly it may take a long time to measure an ionic current or variation may occur. On the contrary, when the diameter of through hole 109 is larger than 10 μm, a space is formed between specimen 112 and through hole 109, or specimen 112 may be sucked into through hole 109, thus reducing a seal resistance value. In this exemplary embodiment, the diameter of through hole 109 is 2.0 μm. The diameter of through hole 109 can be appropriately adjusted to a diameter suitable for capturing specimen 112.

Furthermore, it is desirable that the length of through hole 109 is the same length as the thickness of diaphragm 106. When through hole 109 is too long, second electrolytic solution 104 cannot easily reach specimen 112. Therefore, it is desirable that the length is not less than 5 μm and not more than 20 μm. When the thickness of diaphragm 106 is larger than 20 μm, it is possible to hollow second surface 111 side in a dome shape by etching such that the thickness of diaphragm 106 corresponds to the suitable length of through hole 109. In this exemplary embodiment, the length of through hole 109 and the thickness of diaphragm 106 agree with each other at 10 μm.

Note here that in through hole 109, the opening diameter in first surface 110 of diaphragm 106 and the opening diameter in second surface 111 of diaphragm 106 are different from each other. For example, the opening diameter in second surface 111 of diaphragm 106 may be longer than the opening diameter in first surface 110 of diaphragm 106. Thus, when an agent or the like is allowed to flow into flow passage 105, the agent can reach specimen 112 held inside through hole 109 more efficiently. Alternatively, a recess (not shown) may be formed on second surface 111 of diaphragm 106 so as to communicate with through hole 109. In this case, the same effect can be obtained.

Note here that it is desirable that second surface 111 of diaphragm 106 is provided at the opposite side to first surface 110, but regions on the both ends of through hole 109 are only required to be separated from each other. For example, second surface 111 and first surface 110 may be formed such that they intersect with each other at an arbitrary angle, and through hole 109 may be curved in diaphragm 106.

As a base material for forming diaphragm 106 of sensor chip 101, it is possible to use, for example, a SOI (Silicon on Insulator) substrate in which a silicon layer to be used for diaphragm 106 includes silicon (100). The SOI substrate has a three-layered structure of silicon layer 115a-silicon dioxide layer 115b-silicon layer 115a The SOI substrate is subjected to fine processing by using photolithography and an etching technique, and thereby a large number of highly precise sensor chips 101 can be produced at one time. When the SOI substrate is subjected to etching process, since silicon dioxide layer 115b can function as an etching stop layer, highly precise sensor chip 101 can be produced.

Furthermore, it is desirable that oxide film 116 is formed between noncrystalline solid layer 117 and the SOI substrate of diaphragm 106, that is, on the lower surface layer of noncrystalline solid layer 117. It is preferable that oxide film 116 includes, for example, silicon dioxide.

When oxide film 116 is formed on the entire surface of the SOI substrate provided with through hole 109, wall layer 113, and concave portion 114, the surface of diaphragm 106 becomes an electric insulating material. Oxide film 116 can be formed by using a thermal oxidation method, and by heating at 1100° C. under atmosphere of oxygen and water vapor. The necessary thickness of an oxide film can be appropriately determined but it is generally 500 to 1000 nm.

Note here that noncrystalline solid layer 117 may not be formed in a part of sensor chip 101. However, it is preferable that silicon dioxide layer 115b or oxide film 116 is formed on the outermost surface on which noncrystalline solid layer 117 is not formed.

When silicon dioxide layer 115b or oxide film 116 is formed on the outermost surface of diaphragm 106 on which noncrystalline solid layer 117 is not formed, they are extremely hydrophilic. Therefore, generation of air bubbles at the time of measurement can be suppressed and air bubbles can be removed easily. Consequently, highly precise measurement can be realized. When air bubbles remain in the vicinity of through hole 109 during measurement, the gigaseal property is largely deteriorated, thus making a large effect on the measurement accuracy.

The thickness of silicon dioxide layer 115b is preferably not less than 0.5 μm and not more than 20 μm from the viewpoint of the thickness necessary as an etching stop layer and of the productivity. Note here that silicon dioxide layer 115b of the SOI substrate can be used as oxide film 116.

Note here that sensor chip 101 does not necessarily include wall layer 113 and concave portion 114. Sensor chip 101 may be appropriately selected in a predetermined dimension based on shapes and structures of sensor chip 101. Sensor chip 101 only needs to include diaphragm 106 including at least first surface 110 and second surface 111, as well as through hole 109 penetrating diaphragm 106 so as to link from first surface 110 to second surface 111. That is to say, sensor chip 101 may be in a flat shape.

However, when the thickness of diaphragm 106 is made to be several μm, it is desirable that wall layer 113 is formed with handling and a mounting property in the manufacturing process taken into consideration. That is to say, wall layer 113 functions as a holding portion of sensor chip 101 and enhances the mechanical strength. Furthermore, concave portion 114 functions as storage of liquid. Therefore, it is desirable that wall layer 113 and concave portion 114 are formed.

The holding portion including wall layer 113 can be formed by a method by etching from the SOI substrate or sticking, but etching from the SOI substrate is preferable from the viewpoint of consistency of process.

When the thickness of diaphragm 106 is increased, diaphragm 106 does not easily crack. However, time necessary for processing becomes longer. Therefore, the thickness of diaphragm 106 is desirably thin from the viewpoint of the throughput of steps. Furthermore, when the thickness of diaphragm 106 is increased, the length of through hole 109 is increased. Consequently, the flow passage resistance at the time when specimen 112 is adsorbed by pressure is increased, and specimen 112 is not easily sucked, and the success rate of measurement is reduced. Therefore, the thickness of diaphragm 106 is desirably not less than 5 μm and not more than 50 μm, and further desirably not less than 5 μm and not more than 20 μm.

From the above description, as silicon layer 115a to be used for diaphragm 106 for forming sensor chip 101, a SOI substrate including silicon (100) is selected. However, a silicon (110) substrate, a silicon (111) substrate and silicon substrates having other plane orientations, a glass substrate, and film resin, and the like.

However, from the viewpoint of the workability and the versatility, a substrate including silicon (100) is preferably used. The substrate including silicon (100) may be not only a substrate made of a simple substance of silicon (100) but also a substrate including at least silicon (100). As silicon layer 115a to be used for diaphragm 106, a SOI substrate using silicon (100), a substrate partially or entirely doped with elements such as boron, or a substrate formed by sticking silicon (100) to glass or the like, may be used.

Note here that silicon dioxide layer 115b that functions as an etching stop layer is generally a silicon dioxide layer formed by thermal oxidation. However, it may be silicon dioxide layers formed by other methods such as a CVD method, a sputtering method, a CSD method, or the like, and doped-oxide layers such as a so-called PSG layer doped with phosphorus, a so-called BSG layer doped with boron, or a BPSG layer doped with phosphorous and boron.

In this exemplary embodiment, concave portion 114 is formed from a SOI substrate by dry etching, and at this time, silicon dioxide layer 115b is used as an etching stop layer. Therefore, the surface of concave portion 114 is formed of silicon dioxide layer 115b. However, when the PSG layer, the BSG layer or the PBSG layer are used as the etching stop layer, it is desirable that oxide film 116 is provided on the surface of concave portion 114 by thermal oxidation.

Then, the upper surface of oxide film 116 formed on sensor chip 101, that is, first surface 110 of diaphragm 106 is covered with noncrystalline solid layer 117 made of SiOX. In general, substance X to be introduced in addition to silicon and oxygen is a substance whose electronegativity is higher than that of silicon, and examples thereof include nitrogen, phosphorus, fluorine, boron, and the like. The electronegativity of silicon is 1.90, and the electronegativity of nitrogen, phosphorous, fluorine, and boron is 3.04, 2.19, 3.98, and 2.04, respectively.

Furthermore, it is preferable that substance X has a composition ratio in terms of the number of atoms of not less than 3% and not more than 40%, and further preferably not less than 3.6% and not more than 30% in the outermost surface of noncrystalline solid layer 117.

Note here that the composition ratio in terms of the number of atoms can be calculated based on the number of atoms measured by a technique for identifying the number of atoms by XPS (X-ray Photoelectron spectroscopy).

Note here that an oxynitride film including nitrogen as substance X is used as noncrystalline solid layer 117 for covering, the oxynitride film is formed by thermal nitridation of silicon dioxide layer 115b (or oxide film 116). The thermal nitridation is carried out by calcining sensor chip 101 in an atmosphere of ammonia at high temperature of 1100° C. When first surface 110 of diaphragm 106 is analyzed by XPS, the composition of substances of first surface 110 includes silicon, oxygen, and nitrogen, and the composition ratio in terms of the number of atoms is about 1:1:1.

Herein, the composition ratio in terms of the number of atoms uses a composition ratio, which has been calculated based on the number of atoms measured by a technique for identifying the number of atoms by XPS, and the like, but it can be described by a method for converting the atomic ratio density on the surface.

Zhuravlev et al. has clarified that about 7.9 Si atoms/nm$^2$ are present in the outermost surface of noncrystalline SiO$_2$. Furthermore, one Si atom includes four bonding arms, but the bonding arm that can be out to the outside of the outermost layer is one. That is to say, in noncrystalline SiOX of this exemplary embodiment, the number of bonding molecules (for example, an OH group and an NH$_2$ group, a CH$_3$ group, and the like) existing in an area region of 1 nm$^2$ in the outermost layer is 7.9 molecules at maximum. Based on these, the relation between the number of atoms existing in 1 nm$^2$ of the outermost layer when X of SiOX is N, and the number of atoms (%) calculated by a method for identifying the number of atoms is calculated. The results of calculation of are shown in Table 1. However the number of atoms to be counted is assumed to be in only one layer of the outermost layer.

TABLE 1

| | | Number of atoms per 1 nm$^2$ | | | | Number of atoms % | | | |
|---|---|---|---|---|---|---|---|---|---|
| | | Si | O (*1) | O (*2) | N | Si | O (*1) | O (*2) | N |
| Sample A | SiO$_2$ | 7.9 | 15.8 | 0.0 | 0.0 | 33.3 | 66.7 | 0.0 | 0.0 |
| Sample B | SiO$_2$ + SiOH | 7.9 | 11.9 | 7.9 | 0.0 | 28.6 | 42.9 | 28.6 | 0.0 |
| Sample C | SiON | 7.9 | 11.9 | 0.0 | 7.9 | 28.6 | 42.9 | 0.0 | 28.6 |
| Sample D | SiON + SiOH | 7.9 | 11.9 | 4.0 | 4.0 | 28.6 | 42.9 | 14.3 | 14.3 |
| Sample E | SiON + SiOH | 7.9 | 11.9 | 6.9 | 1.0 | 28.6 | 42.9 | 25.0 | 3.6 |

(*1): siloxane-derived
(*2): silanol-derived

Sample A includes only SiO$_2$, and all the outermost layer is siloxane-bonded (Si.O.Si). In sample A, no OH groups are present on the surface. At this time, the number of atoms (%) is 33.3% for Si and 66.7% for O.

Sample B includes SiO$_2$, and is in the most hydrophilic state in which OH groups are formed on all the Si atoms in the outermost layer. At this time, the number of atoms (%) is 28.6% for Si, 42.9% for O (siloxane derived) and 28.6% for O (silanol derived).

Sample C is an example of noncrystalline SiOX in this exemplary embodiment. In a configuration in which substance X is N, all the Si bonding arms of the outermost layer are terminated in NH$_2$ molecule. At this time, the number of atoms (%) is 28.6% for Si, 42.9% for O (siloxane derived), and 28.6% for N.

Sample D is an example of noncrystalline SiOX in this exemplary embodiment. In the configuration in which substance X is N, the half of the Si bonding arms of the outermost layer is terminated in an NH$_2$ group, and the rest half is terminated in an OH group. At this time, the number of atoms (%) is 28.6% for Si, 42.9% for O (siloxane derived), 14.3% for O (silanol derived), and 14.3% for N.

Sample E is one example of noncrystalline SiOX in this exemplary embodiment. In the configuration in which substance X is N, one of the Si bonding arms of the outermost layer is terminated in an NH$_2$ group, and the rest is terminated in an OH group. At this time, the number of atoms (%) is 28.6% for Si, 42.9% for O (siloxane derived), 25% for O (silanol derived), and 3.6% for N.

In the above, when the relation between the number of atoms and the number of atoms % is used, the composition ratio in terms of the number of atoms of not less than 3.6% and not more than 30% corresponds to the number of NH$_2$ existing in 1 nm$^2$ of the outermost layer of not less than one and 7.9 at maximum.

Note here that the calculation of the number of atoms % in Table 1 is carried out as to the arrangement of atoms existing on the surface of noncrystalline SiO$_2$ in a Zhuravlev model in an ideal state of some cases of molecule modification that can be taken on the surface. The calculated numeric value is round off to the first decimal place. Therefore, a case in which the total cannot be 100% may occur, but there is no problem because it is a calculation error.

Furthermore, the above-mentioned calculation is carried out in an ideal state. Actually, factors of errors including a crystal defect, crystal distortion, a measuring apparatus error, surface contamination, and the like, may occur. Therefore, the number of atoms %, which is measured and identified by XPS, cannot not always be measured at this accuracy.

As substance X of SiOX, N is described, but other elements providing the same effects are present as mentioned below.

In FIG. 2B, since an oxynitride film as noncrystalline solid layer 117 is formed by thermal nitridation, noncrystalline solid layer 117 is formed not only on the surface of diaphragm 106 but also on the entire surface of sensor chip 101. The entire surface of sensor chip 101 includes the surface of through hole 109. In other words, noncrystalline solid layer 117 is formed also on the wall surface of through hole 109.

Figure 2C:
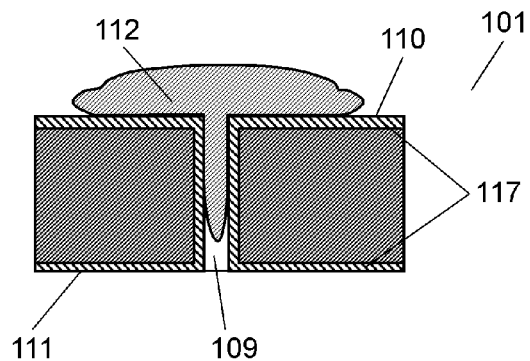
FIG. 2C is a sectional view showing a principal part of the single-hole sensor chip in accordance with the exemplary embodiment of the present invention.

In a state in which specimen 112 is sucked on through hole 109 as shown in FIG. 2C, a part of specimen 112 is sucked to through hole 109. Therefore, the cell membrane of specimen 112 is widely brought into contact with the inner surface of through hole 109. Therefore, the affinity between through hole 109 and specimen 112 is important for the sealing property.

In the film formation method using, for example, an LPCVD method, since substances of noncrystalline solid layer 117 are piled in the anisotropic direction, it is extremely difficult to cover the entire surface of sensor chip 101 including the inner surface of through hole 109.

Figure 3:
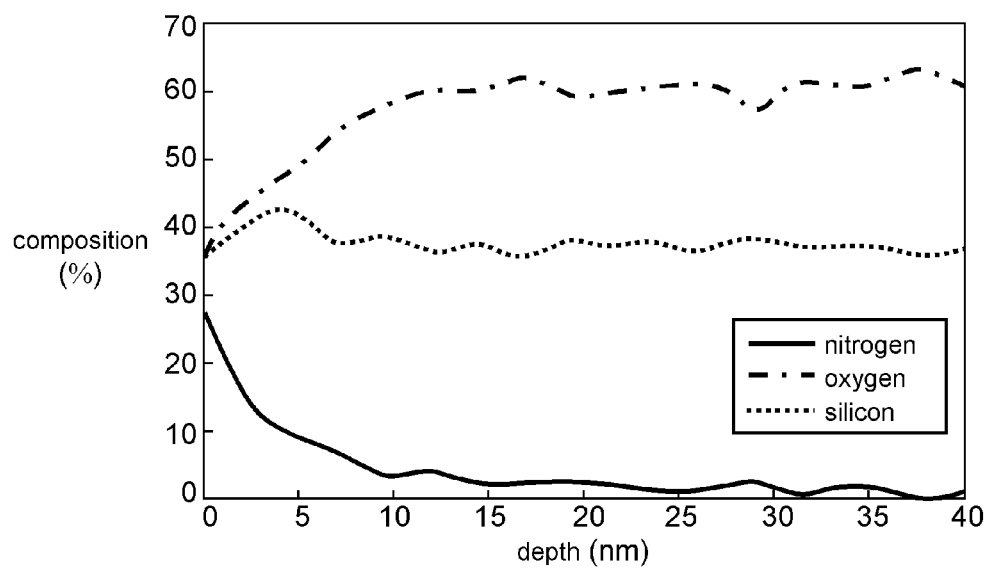
FIG. 3 is a graph showing a change of distribution of compositions in the thickness direction of a diaphragm of the sensor chip in accordance with the exemplary embodiment of the present invention.

FIG. 3 is a graph showing a change of distribution of compositions in the thickness direction of the diaphragm of the sensor chip in accordance with the exemplary embodiment of the present invention. For a material to be measured, below-mentioned sample 2 is used. The changes of the compositions of silicon, oxygen and nitrogen in the diaphragm in the thickness direction are examined by XPS, and the results are shown. FIG. 3 shows that a layer containing nitrogen does not have a constant thickness, but shows distribution in which the composition ratio in terms of the number of atoms of nitrogen is reduced substantially exponentially to a place having a thickness of about 10 nm from the outermost surface of noncrystalline solid layer 117 without having an inflection point. From the outermost surface that is rich in nitrogen of noncrystalline solid layer 117 to silicon dioxide layer 115b (or oxide film 116) that is silicon dioxide, compositions are continuously changed without having a specifically clear interface. Thus, it is estimated that the inner stress due to lattice mismatch and the like on the interface is relieved, and a physically stable structure is realized.

Figure 4:
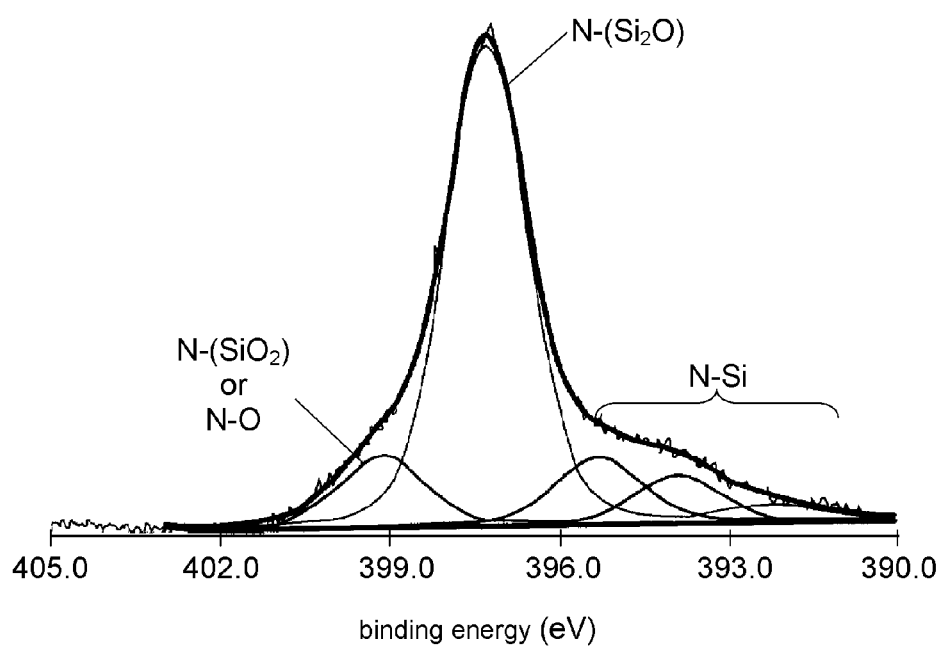
FIG. 4 is a graph showing a core level photoelectron spectrum of nitrogen is by XPS on a surface of the diaphragm of the sensor chip in accordance with the exemplary embodiment of the present invention.

FIG. 4 is a graph showing a core level photoelectron spectrum of nitrogen 1s by XPS on the surface of the diaphragm of the sensor chip in accordance with the exemplary embodiment of the present invention. As a material to be measured, the below-mentioned sample 2 is used. The graph shows the core level photoelectron spectrum of nitrogen 1s (N1s) of first surface 110 obtained by XPS. A peak is shown in the center part and skirt-like structures are shown in both sides. This is decomposed into the superposition of some peak components. In general, a single photoelectron peak by an XPS peak can be represented by a combination of the Gaussian function and the Lorentz function. Therefore, when fitting is carried out in a function in which 20% or Lorentz function is superimposed onto the Gaussian function, superimposition of five peaks can be expressed as shown in FIG. 4. When attribution of each peak is identified, it is shown that the highest peak in the middle portion and a peak at the side at which the binding energy is higher are attributed to a silicon oxynitride film. In a silicon nitride layer formed by a general LPCVD method, mainly $Si_3N_4$ layer is shown, which is different from the oxynitride film formed by the thermal nitridation process used in the present invention.

Property of the cell electrophysiological measurement device using sensor chip 101 configured as mentioned above is described hereinafter.

In order to examine the surface composition of diaphragm 106 of sensor chip 101, a large number of experimentally produced sensor chips 101, in which diaphragm 106 is subjected to various surface modification processes, are produced and evaluated. In the evaluation experiment, a plate on which 96 pieces of cell electrophysiological measurement devices shown in FIG. 1 are formed in matrix is produced, and an electrical resistance value (a seal resistance value) between first electrode 107 and second electrode 108 is measured in a state in which specimen 112 is held in through hole 109 of diaphragm 106.

Sensor chip 101 that is used in the experiment is subjected to the below-mentioned treatment.

In sample 1, oxide film 116 is formed by thermal oxidation process in which heating is carried out at 1100° C. in the atmosphere of oxygen and water vapor, and then washing with ammonium fluoride buffered hydrofluoric acid solution is carried out. Furthermore, ashing treatment with oxygen plasma (oxygen ashing) is carried out.

In sample 2, oxide film 116 is formed by thermal oxidation process in which heating is carried out at 1100° C. in the atmosphere of oxygen and water vapor, and then an oxynitride film as noncrystalline solid layer 117 is formed by thermal nitridation in which heating is carried out at 1100° C. in the atmosphere of ammonia.

In comparative sample 1, oxide film 116 is formed by thermal oxidation process in which heating is carried out at 1100° C. in the atmosphere of oxygen and water vapor.

In comparative sample 2, oxide film 116 is formed by thermal oxidation process in which heating is carried out at 1100° C. in the atmosphere of oxygen and water vapor, and then washing with an ammonium fluoride buffered hydrofluoric acid solution is carried out.

These samples are mounted on a plate, that is, 96 wells 102, and a seal resistance value is measured. The measuring procedure is as follows.

Step 1: Phosphate buffered saline (PBS) is used as first electrolytic solution 103, and a RBL (Rat Basophilic Leukemia) cell line as specimen 112 is dispensed in each well 102.

Step 2: As second electrolytic solution 104, an aqueous solution of NaCl, potassium gluconate, chelate agent (EDTA-NaCl) and a buffer solution (HEPES-NaCl) is filled in flow passage 105.

Step 3: A negative pressure is applied to well 102 from flow passage 105 via through hole 109, specimen 112 is sucked and held in through hole 109. After passage of two minutes, an electrical resistance value (a seal resistance value) between first electrode 107 and second electrode 108 is measured.

Step 4: Antibiotics reagent to be used for perforated patch is added in second electrolytic solution 104 so as to form micropores in the cell membrane of specimen 112 in through hole 109. Thus, a whole cell state is formed and a seal resistance value is measured.

Figure 5:
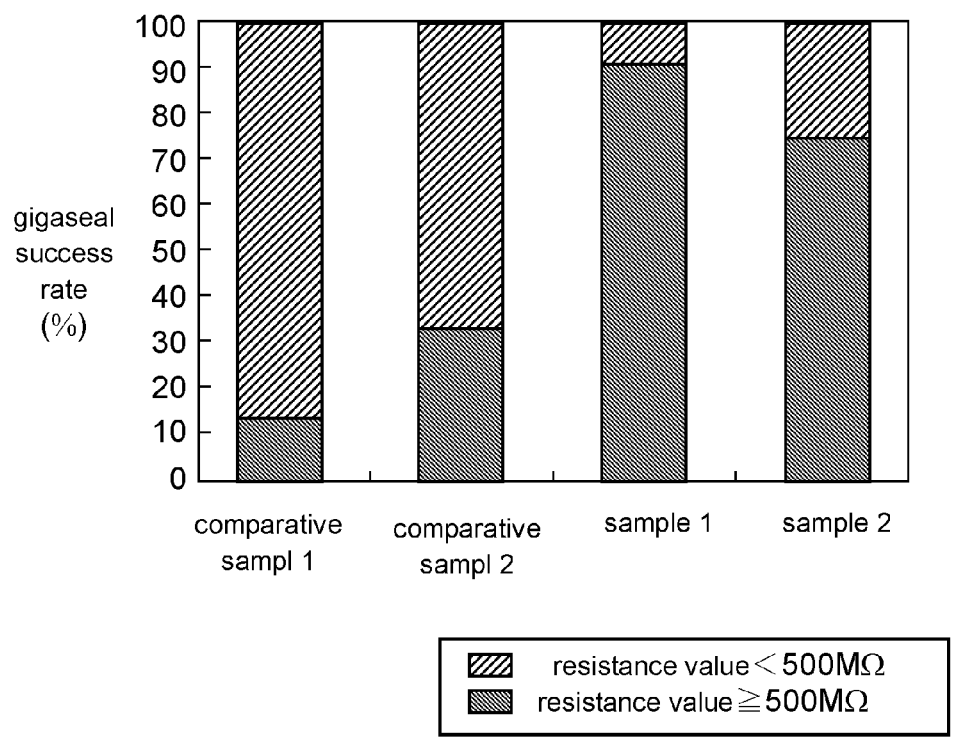
FIG. 5 is a graph showing a gigaseal success rate of the sensor chip in accordance with the exemplary embodiment of the present invention.

FIG. 5 is a graph showing a gigaseal success rate in accordance with the exemplary embodiment of the present invention. Seal resistance values of comparative samples 1 and 2 and samples 1 and 2 are measured. The resistance values measured as to 96 wells 102 are shown in bar graphs showing success of gigaseal and not success of gigaseal. Herein, sensor chip 101 exhibiting a seal resistance value of not less than 500 mΩ is determined to be success of gigaseal. From FIG. 5, in untreated comparative sample 1 in which only a thermal oxidation film is formed, the gigaseal success rate is ten-something %. However, it is shown that when BHF washing treatment (comparative sample 2) and oxygen ashing treatment (sample 1) are added, the gigaseal success rate is improved.

This can be described as follows. In the comparative sample, when a surface after oxide film 116 is formed by thermal oxidation is subjected to BHF washing, oxide film 116 on the surface is weakly etched. At this time, since contaminants attached on the surface are removed, adhesion with respect to specimen 112 is improved, and the gigaseal success rate is increased. However, since the surface of oxide film 116, which has been subjected to BHF treatment, includes a large number of hydrogen terminated silicon atoms, the surface has a low hydrophilic property and has insufficient affinity with respect to hydrophilic specimen 112. Then, as shown in sample 1, the oxygen ashing treatment is carried out, so that the terminal is replaced by a hydroxyl group and the surface becomes hydrophilic. Thereby, the affinity with respect to the cell membrane is improved and the gigaseal success rate is increased. The oxygen ashing has also an effect of promoting removal of carbon-based contaminants.

Although sample 2 is inferior in the sealing property as compared with sample 1, excellent gigaseal success rate can be obtained.

In this exemplary embodiment, the surface of first surface 110 is not a silicon nitride film $Si_3N_4$ obtained by a process such as LPCVD, but a silicon oxynitride film (oxynitride film) obtained by thermal nitridation. Thus, by changing the ratio of oxygen and nitrogen, the surface activity or surface potential can be controlled. Furthermore, it is possible to suppress physical instability caused by discontinuity due to lattice mismatch and the like between the surface and silicon dioxide forming silicon dioxide layer 115b or silicon dioxide forming oxide film 116. Thus, sensor chip 101 whose surface is stable can be formed. Furthermore, since a silicon oxynitride film by thermal nitridation has a nitrogen concentration that is continuously changed in the depth (thickness) direction, the internal stress can be reduced. Then, by treating an oxynitride film as the formed noncrystalline solid layer 117 with acid or plasma, for example, a silanol group (Si.OH) can be easily formed on the surface. Therefore, various surface modifications can be carried out as compared with a $Si_3N_4$ layer.

Figure 6:
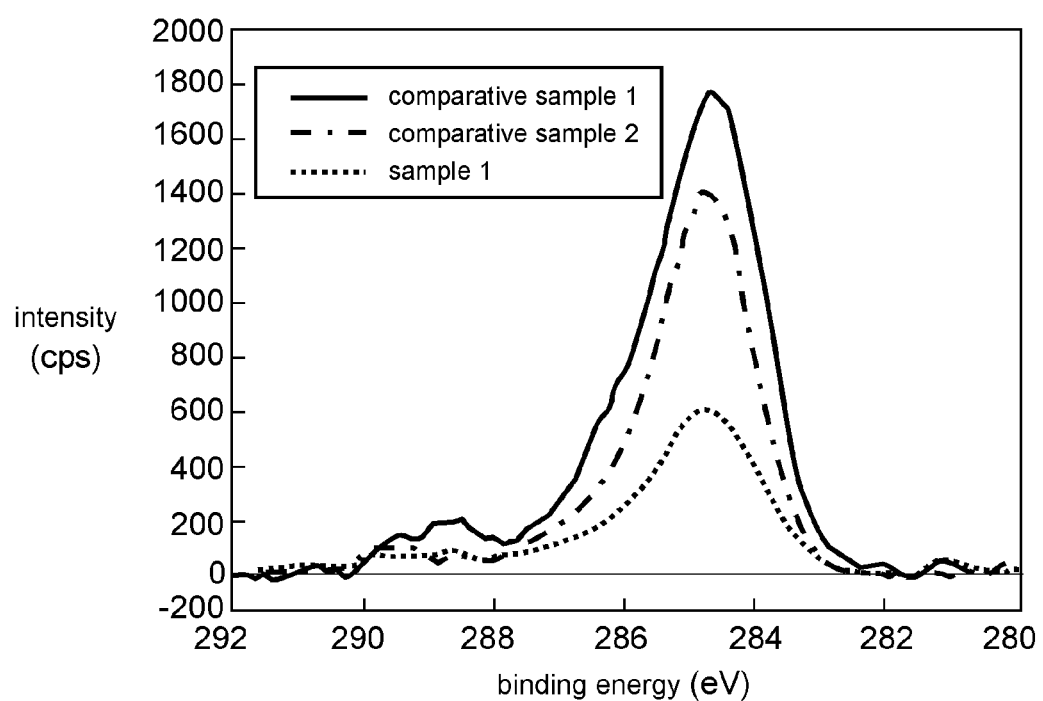
FIG. 6 is a graph showing a carbon is core level spectrum by XPS on an oxide film surface of the sensor chip in accordance with the exemplary embodiment of the present invention.

FIG. 6 is a graph showing results of examination by XPS of an existing amount of carbon is (Cis) as contaminants on the surface of diaphragm 106 in comparative samples 1 and 2 and sample 1. Carbon is a typical contaminant found in the case where a test material is left in the air in, for example, a clean room. Also from FIG. 6, it can be recognized that carbon on diaphragm 106 is reduced by BHF washing and oxygen ashing treatment.

The property of sample 1 in which the gigaseal success rate of not less than 500 MΩ is more than 90% is sufficiently satisfactory as the initial property. However, after measurement plates on which the manufactured sensor chips 101 are mounted on well 102 are mass-produced and shipped, they are required to be maintained to have an excellent sealing property for a long period of time.

The present inventors evaluate the change in the sealing property after storage for a predetermined time in sensor chip 101 that has been subjected to the same treatment as in sample 1 in which excellent property is obtained in the above-mentioned experiment. Herein, for storage, a nitrogen desiccator in which nitrogen gas is allowed to always flow into a sealed container is used.

Figure 7:
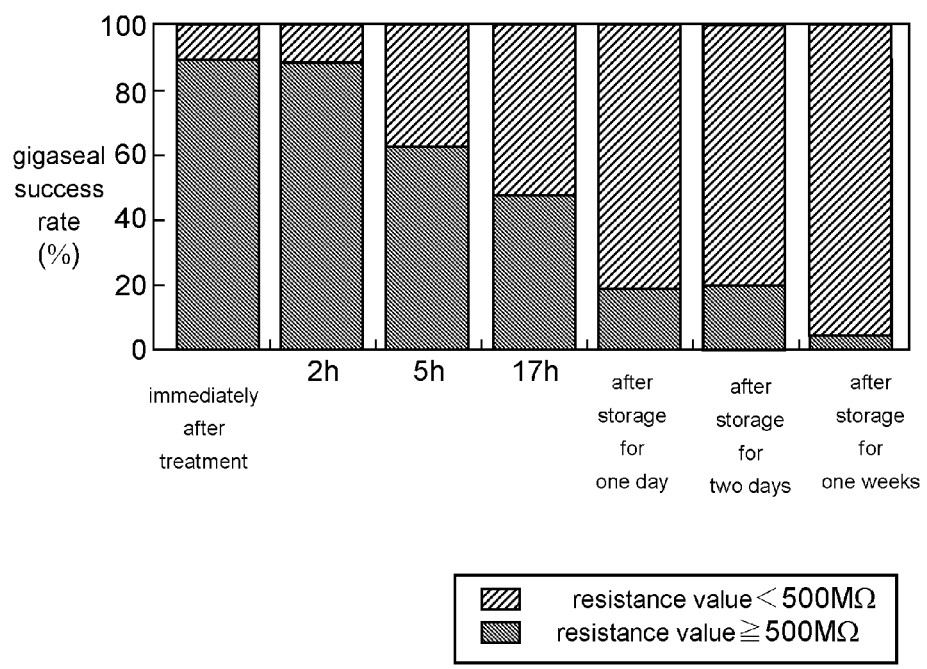
FIG. 7 is a graph showing a change of the gigaseal success rate with respect to a storage time in the sensor chip in accordance with the exemplary embodiment of the present invention.

FIG. 7 is a graph showing a relation between a storage time and a gigaseal success rate of sample 1. The axis of abscissas of the graph shows a passage time after the oxygen ashing treatment similar to that of sample 1 is carried out and measurement of seal resistance is carried out. The gigaseal success rate already starts to be reduced when five hours have passed after the oxygen ashing treatment is carried out, and the success rate is suddenly reduced to about 20% in one day.

This is thought to be as follows. The surface of oxide film 116 of diaphragm 106 which is subjected to oxygen ashing treatment is in a state in which surface energy is extremely high, and contaminants in storage atmosphere are easily adsorbed. Therefore, contamination on the surface proceeds as passage of time, and thus the sealing property is reduced. Herein, the contaminant is estimated to be an organic compound. Furthermore, silanol groups (Si.OH) existing in the surface of the oxide film after oxygen ashing are easily dehydrated in the air so as to be changed into siloxane, and then the hydrophilic property is lost. Note here that the atmosphere is not limited to the air and it may be atmospheres of nitrogen or other inert gases or a vacuum state. In such cases, similar dehydration occurs. Therefore, it is estimated that reduction in the affinity between the specimen and the cell membrane is thought to be a cause of deterioration of the sealing property. The reduction cannot be completely prevented even in environments such as a nitrogen atmosphere and in a vacuum state.

Figure 8:
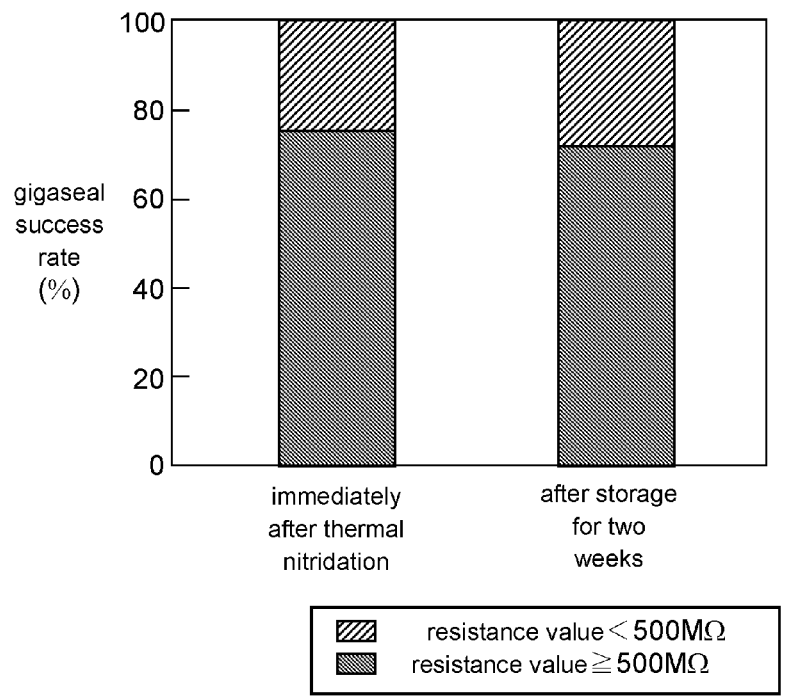
FIG. 8 is a graph showing a change of the gigaseal success rate depending upon a storage time in accordance with the exemplary embodiment of the present invention.

FIG. 8 is a graph showing a change of the gigaseal success rate of sample 2 with respect to the storage time. Storage is carried out in a nitrogen desiccator as in the case of FIG. 7. FIG. 8 shows a graph showing a sealing property of sensor chip 101 by sample 2 immediately after thermal nitridation treatment is carried out as nitriding treatment, and after storage in the nitrogen desiccator for two weeks. As is apparent from comparison with the results of sample 1 shown in FIG. 7, in sample 2 of FIG. 8, the initial gigaseal success rate is maintained even after two weeks of storage. Thus, the storage property is dramatically improved.

Note here that a test of the above-mentioned deterioration degree is carried out by using a RBL-1 cell. However, since the deterioration degree varies depending upon types and states of cells to be measured, how long the deterioration lifetime is increased cannot be indiscriminately determined. However, it is clear that treatment used for sample 2 slows the time taken for deterioration as compared with the treatment used for sample 1.

As in sample 1, in the environment that is near an oxide film, that is, in a state in which no or few N bonds are present, even in the same environment, a hydrophilic property is easily deteriorated. That is to say, SiOH is easily dissociated. In sample 1, in order to maintain the initial gigaseal success rate, it is necessary to carry out underwater storage or vacuum package, or the like. Package using a freezing container or a cold insulator is necessary, and furthermore, special concern is required for transportation. Thus, cost is increased. However, by employing the configuration of sample 2, storage and transportation can be carried out while the initial property is maintained as compared with sample 1 even at ordinary temperature (25° C.), thus significantly reducing the package and transportation cost.

Furthermore, sensor chip 101 of sample 2 is not washed by, for example, BHF washing or oxygen plasma treatment before thermal nitridation treatment is carried out. There are many factors for increasing cost, for example, BHF is highly dangerous and it requires protective steps, and a plasma generating apparatus is expensive and its process takes a long time. However, sample 2 is advantageous because it does not have such factors for increasing cost.

Note here that in this exemplary embodiment, noncrystalline solid layer 117 is formed also on both surfaces of first surface 110 and second surface 111 of diaphragm 106 and inner wall surface of through hole 109. However, the configuration is not necessarily limited to this. For example, noncrystalline solid layer 117 may be formed only on first surface 110. In this case, for example, when thermal nitridation treatment is carried out, it is not necessary to consider a fixing method of sensor chip 101 of exposing second surface 111 side to the atmosphere, so that the process becomes easy and simple. Alternatively, noncrystalline solid layer 117 may be formed on both first surface 110 and second surface 111. Alternatively, noncrystalline solid layer 117 may be formed only on the wall surface of the through hole.

However, an oxynitride film as noncrystalline solid layer 117 is formed on all over the entire surface of sensor chip 101, and thereby electric insulation on the surface of sensor chip 101 can be strong. Furthermore, stress applied to both surfaces of first surface 110 and second surface 111 of diaphragm 106 can be equalized. Therefore, diaphragm 106 can be made to be physically stable.

Second Exemplary Embodiment

Figure 9:
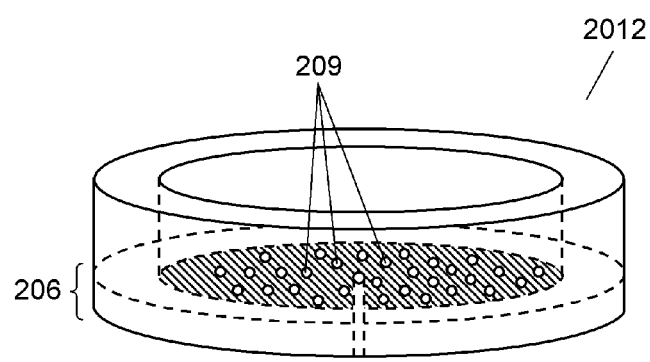
FIG. 9 is a perspective view of a multi-hole sensor chip in accordance with an exemplary embodiment of the present invention.

Hereinafter, a cell electrophysiological measurement device of a second exemplary embodiment of the present invention is described with reference to drawings. FIG. 9 is a perspective view of a multi-hole sensor chip in accordance with the exemplary embodiment of the present invention.

In this exemplary embodiment, the same reference numerals are given to the same configurations as in the first exemplary embodiment and detailed description thereof is omitted. A cell electrophysiological measurement device using multi-hole sensor chip 2012 including a plurality of through holes 209 on diaphragm 206 is described.

In this exemplary embodiment, diaphragm 206 provided with 64 through holes 209 is used. The number of through holes 209 can be selected arbitrarily. Multi-hole sensor chip 2012 can be formed by using similar process as in the first exemplary embodiment by changing the number of mask holes in a resist mask formed before through holes 209 are formed. In the second exemplary embodiment, the number of through holes 209 is 64, but the number is not necessarily limited to this. Note here that in FIG. 9, all through holes 209 are not shown in order to avoid complexity. When the number of through holes 209 is increased, since averaged ionic currents can be measured, variation of the ionic channel property of specimens 112 is averaged, and thus measurement success rate and accuracy are improved.

In measurement using a plurality of through holes 209 as in this exemplary embodiment, a seal resistance value as a whole of sensor chip 2012 is expressed as a resistance value of parallel-combined resistance values of seal resistance values of individual through holes 209. Furthermore, in multi-hole sensor chip 2012, data of the ionic current obtained from a plurality of through holes 209 are averaged. Therefore, the limitation of the combined seal resistance value is somewhat relieved as compared with the case where the number of through holes 209 is one. Therefore, in multi-hole sensor chip 2012, it is desirable that the combined resistance (seal resistance) of not less than 100 MΩ is always obtained, or it can be obtained at a percentage of not less than 95%. Note here that this limited numeric value varies depending upon the ratios S/N of current S output from an ionic channel to leakage current N. In other words, it varies depending upon the types of cells, the numeric values are not necessarily limited to the above-mentioned values in this exemplary embodiment.

Hereinafter, an effect of this exemplary embodiment is described with reference to specific examples. In sample 3, treatment shown in sample 1 in the first exemplary embodiment is given to multi-hole sensor chip 2012. That is to say, in sample 3, oxide film 116 is formed by a thermal oxidation process in which heating is carried out at 1100° C. in an atmosphere of oxygen and water vapor, and then washing with an ammonium fluoride buffered hydrofluoric acid solution is carried out. Furthermore, ashing treatment with oxygen plasma (oxygen ashing) is carried out.

Furthermore, in sample 4, treatment shown in sample 2 in the first exemplary embodiment is given to multi-hole sensor chip 2012. That is to say, in sample 4, oxide film 116 is formed by thermal oxidation process in which heating is carried out at 1100° C. in the atmosphere of oxygen and water vapor, and then an oxynitride film as noncrystalline solid layer 117 is formed by thermal nitridation in which heating is carried out at 1100° C. in the atmosphere of ammonia.

Figure 10:
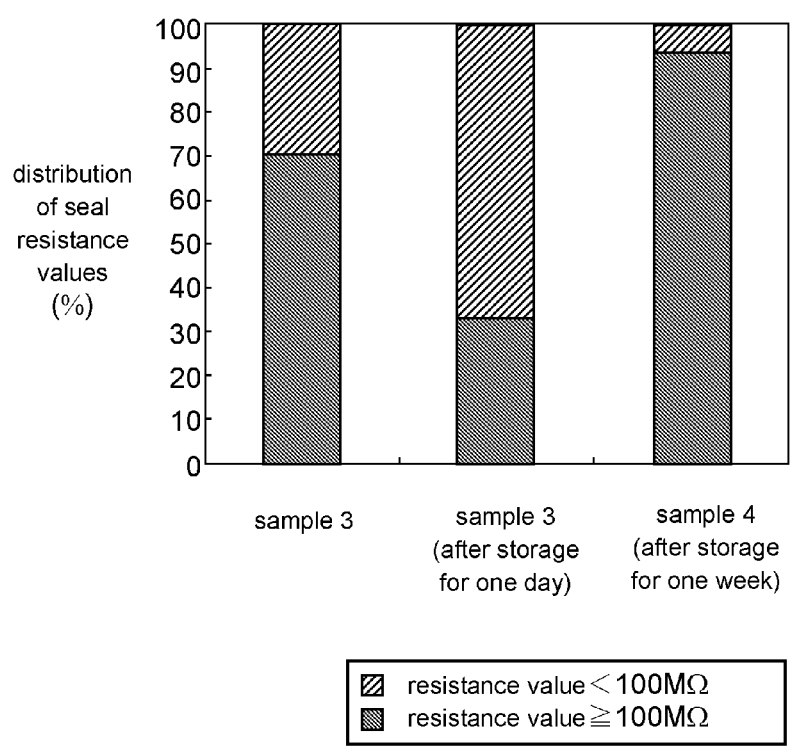
FIG. 10 is a graph showing distribution of seal resistance values in the sensor chip in accordance with the exemplary embodiment of the present invention.

FIG. 10 is a graph showing distribution of seal resistance values of the sensor chips in accordance with the exemplary embodiment of the present invention.

In sample 3, sensor chips 2012 having averaged combined seal resistance of smaller than 100 MΩ occupy about 30% in entire sensor chips 2012. Furthermore, it is increased to 64% when sample 3 is stored in a nitrogen desiccator for one day after the oxygen ashing treatment is carried out.

This is thought to be because the number of through holes in which a specimen is not held correctly is increased as the number of through holes is increased. For example, 64 through holes 209 are provided as in this exemplary embodiment, if the seal resistance of through holes 209 that cannot hold specimen 112 is low as about 10 MΩ, in order to make a combined resistance value of not less than 100 MΩ, the number of through holes 209 having low resistance is not more than one. Furthermore, from calculation results of binomial distribution, for example, for allowing the combined seal resistance of not less than 100 MΩ to succeed at the rate of not less than 95%, the occurrence rate of low-resistance through holes 209 is required to be not more than 0.5% (such things are described later with reference to FIG. 13).

In order to level the ionic channel currents by using a plurality of through holes 209, the number of through holes 209 is preferably large. On the other hand, however, the larger the number of through holes 209 becomes, the more leakage current becomes. When sensor chip 2012 of sample 3 is used, when the success rate of measurement is taken into consideration, the number of more than about 10 is not realistic.

Similar measurement is carried out after sensor chips 2012 of sample 4 are stored in a nitrogen desiccator for a week. The results of the measurement are shown in FIG. 10. In sample 4, although one week has passed after treatment, 95.8% of sensor chips 2012 shows a combined seal resistance value of not less than 100 MΩ.

This is thought to be as follows. Sensor chip 2012 of sample 3 immediately after oxygen ashing treatment is carried out after BHF washing shows a high seal resistance value. Also in FIG. 5, sample 1 that has been subjected to oxygen ashing treatment shows a high seal resistance value. This is thought to be because the affinity between specimen 112 and diaphragm 206 is high. A high seal resistance value can be obtained with respect to specimen 112 correctly held on through holes 209. However, when specimen 112 is placed on through hole 209 incompletely, since the affinity between specimen 112 and diaphragm 206 is too high, specimen 112 cannot move and cannot cover through holes 209 completely. Furthermore, when a cell is used as specimen 112, the cell membrane is broken in the vicinity of through holes 209, fragments of the broken cell membrane cannot move from the periphery of through holes 209. Therefore, even if normal specimen 112 comes to through hole 209, the fragments hinder movement of specimen 112, so that specimen 112 cannot block through-hole 209. As a result, the seal resistance value of through hole 209 is extremely reduced. Since a plurality of such through holes 209 are generated, the possibility that the combined seal resistance of the entire sensor chip 2012 (that is, 64 through holes 209) is reduced becomes high.

On the other hand, in sensor chip 2012 that has been subjected to thermal nitridation treatment, as it is estimated from sample 2 of FIG. 5, the affinity between the surface of specimen 112 and the surface of diaphragm 206 is not so high, and specimen 112 can move to some extent. Accordingly, specimen 112 that is mounted on through holes 209 incompletely is little bit moved by suction, so that specimen 112 blocks through holes 209 completely. Furthermore, even if fragments of the cell membrane are present, since the fragments of the cell membrane are not so strongly attached to the surface of diaphragm 206, they flow to the other place. Holding of specimen 112 is not prevented. With such an effect, through holes 209 showing extremely low seal resistance are hardly generated in sample 4, and the reduction of combined resistance value is suppressed. Sample 4 can maintain the property for a long time as compared with sample 3 even if special treatment such as underwater storage is not carried out.

Note here that a distance between centers of through holes 209 is desirably not less than 20 µm from the viewpoint of the measurement success rate. Although depending upon the types of specimens 112, culture conditions, and the like, a diameter of specimen 112 is generally about 20 µm. Therefore, the interval between through holes 209 is smaller than 20 µm, specimens 112 may interfere with each other, thus reducing the success rate of measurement. On the other hand, by increasing the distance between through holes 209, since structurally weak portions do not easily aggregate densely, the reliability of sensor chip 2012 is improved.

The interval between through holes 209 is preferably equal, and it is desirable that through holes 209 are arranged point-symmetrical with respect to the central point of sensor chip 2012. This is desirable because symmetry occurs in terms of the sucking property when specimen 112 is sucked, and averaged data can be obtained easily.

Third Exemplary Embodiment

Hereinafter, a cell electrophysiological measurement device in accordance with a third exemplary embodiment of the present invention is described with reference to drawings. In this exemplary embodiment, the same reference numerals are given to the same components described in the first and second exemplary embodiments, and the description thereof is omitted.

Figure 11A:
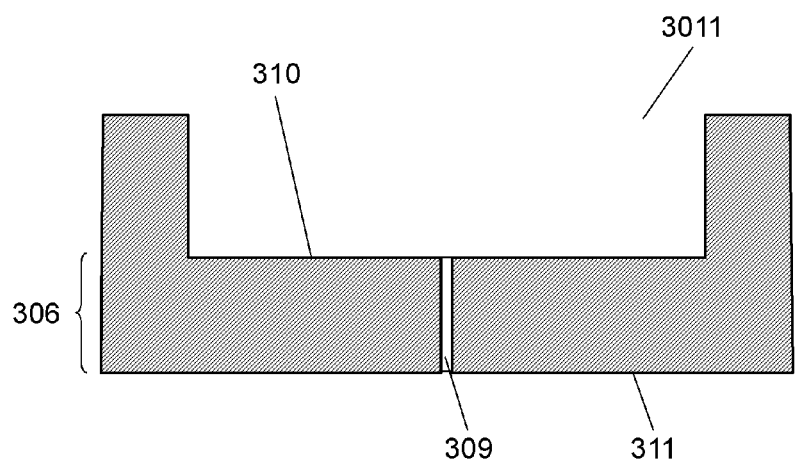
FIG. 11A is a sectional view of a single-hole sensor chip in accordance with an exemplary embodiment of the present invention.
Figure 11B:
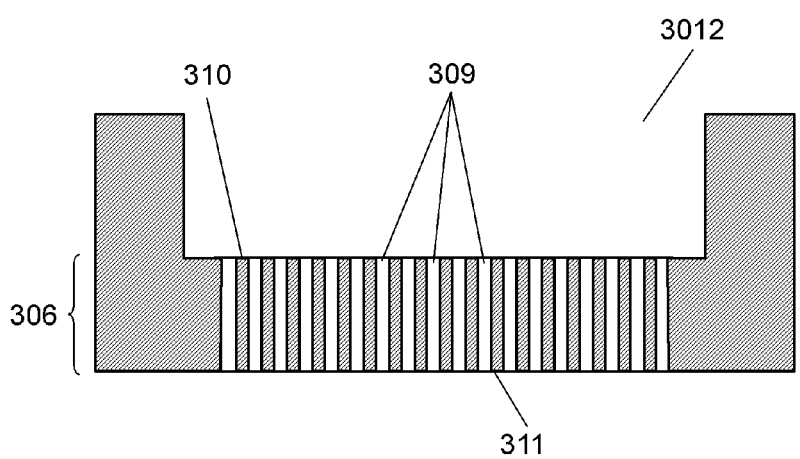
FIG. 11B is a sectional view of a multi-hole sensor chip in accordance with the exemplary embodiment of the present invention.

FIG. 11A is a sectional view of single-hole sensor chip 3011 having one through hole 309 in diaphragm 306. FIG. 11B is a sectional view of multi-hole sensor chip 3012 having a plurality of through holes 309 in diaphragm 306.

In this exemplary embodiment, surface potential of one of the surfaces of first surface 310, second surface 311 and through hole 309 of diaphragm 306 is negative electric potential.

As mentioned below, zeta electric potential of sensor chip 3011, 3012 has high correlation with specimen adhesion and property maintaining rate during long-term storage. For evaluation of the specimen adhesion, measurement of the surface physical property of sensor chip 3011, 3012, that is, the surface zeta electric potential (hereinafter, surface potential) is used. Furthermore, according to the shapes of sensor chips 3011, 3012, a method for optimally treating the surfaces of sensor chip 3011, 3012 is found. The surface used herein includes surfaces of first surface 310, second surface 311, and inner wall of through hole 309.

In single-hole sensor chip 3011, it is preferable that the surface potential is not higher than −20 mV. It is not preferable that the surface potential is higher than −20 mV because the adhesion of cells is weakened, and a gigaseal is not easily formed.

In multi-hole sensor chip 3012, it is preferable that the surface potential is not lower than −20 mV and lower than 0 mV. It is not preferable that the surface potential is lower than −20 mV because a low-resistance component is generated although a gigaseal is easily formed. It is not preferable that the surface potential is higher than 0 mV because a cell adhesion property is low.

Note here that it is desirable that the surface potential of at least first surface 310 or the surface potential of second surface 311 is equal to the surface potential of the inner wall of through hole 309. It is desirable because a state with higher adhesion property can be obtained from the above-mentioned configuration.

The surface potential can be made to be negative electric potential by forming an oxynitride film as shown in, for example, the first exemplary embodiment. Other methods for forming an oxynitride film include a CVD method, a sputtering method, a CSD method, plasma nitridation, thermal nitridation, and the like. An arbitrary method from them may be selected. In particular, thermal nitridation is desirable. By carrying out thermal nitridation, a film is formed on first surface 310 and second surface 311 to uniform film thickness, and as a result, warp of diaphragm 306 can be suppressed. Furthermore, it is desirable that when a film is made to be uniform, diaphragm 306 whose surface potential of first surface 310 is equal to the surface potential of second surface 311 is formed.

Next, the adhesion property between specimen 112 and through hole 309, which is necessary for single-hole sensor chip 3011 and multi-hole sensor chip 3012, is described.

Single-hole sensor chip 3011 is suitable for measurement of an ionic channel through which only a slight amount of electric current flows because a gigaseal state is achieved when specimen 112 is closely attached to through hole 309 with a high adhesion force. However, when a surface hydrophilic property of diaphragm 306 with which specimen 112 is brought into contact is increased, adhesion between specimen 112 and diaphragm 306 is too strong. Therefore, specimen 112 is not accurately captured on through hole 309, and attached to the other places such as the well side surface other than the surface of through hole 309 or a first substrate surface, and specimen 112 that adheres to such places cannot move. As a result, the resistance becomes low of not more than 10 MΩ.

Figure 12:
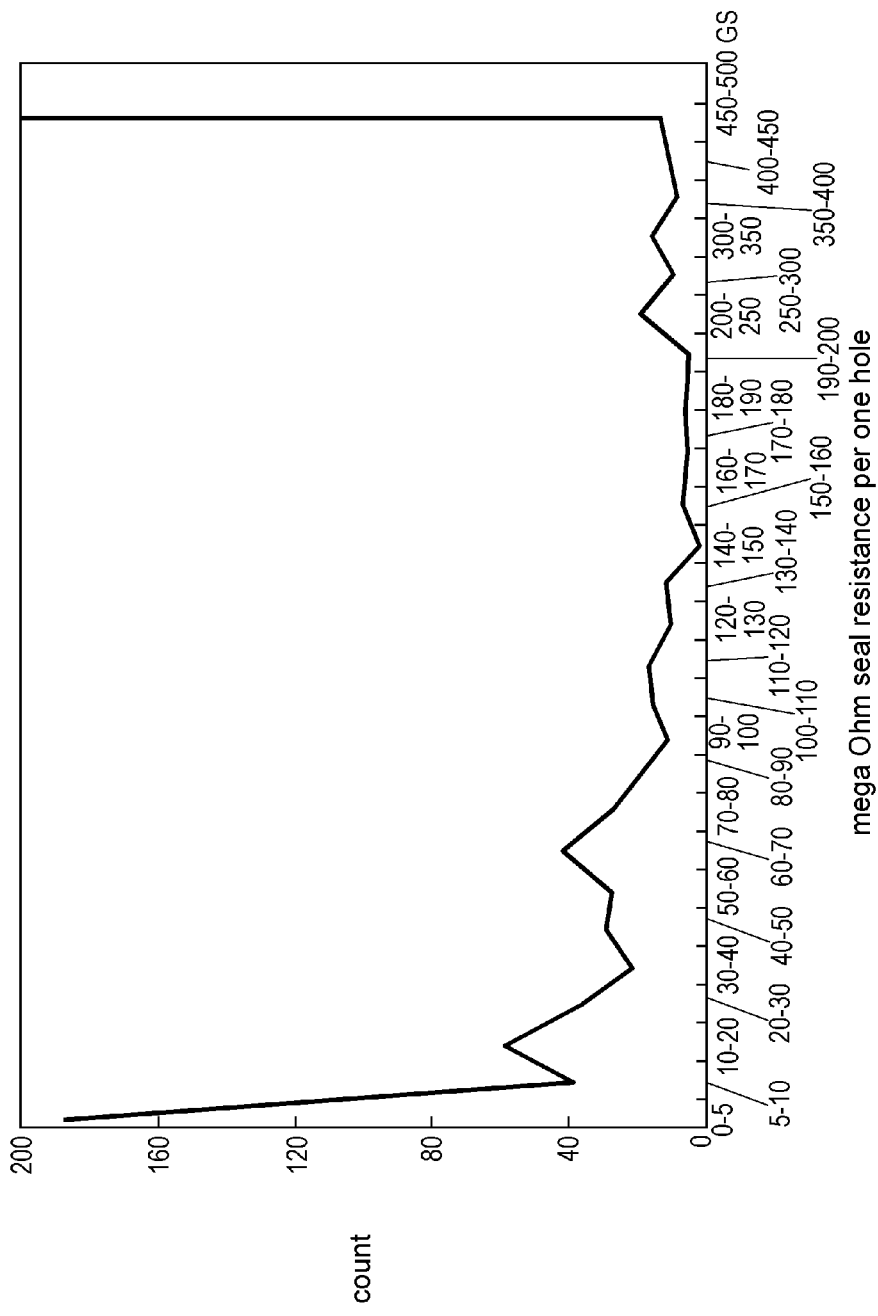
FIG. 12 is a graph showing distribution of seal resistance values of the single-hole sensor chip in accordance with the exemplary embodiment of the present invention.
Figure 13:
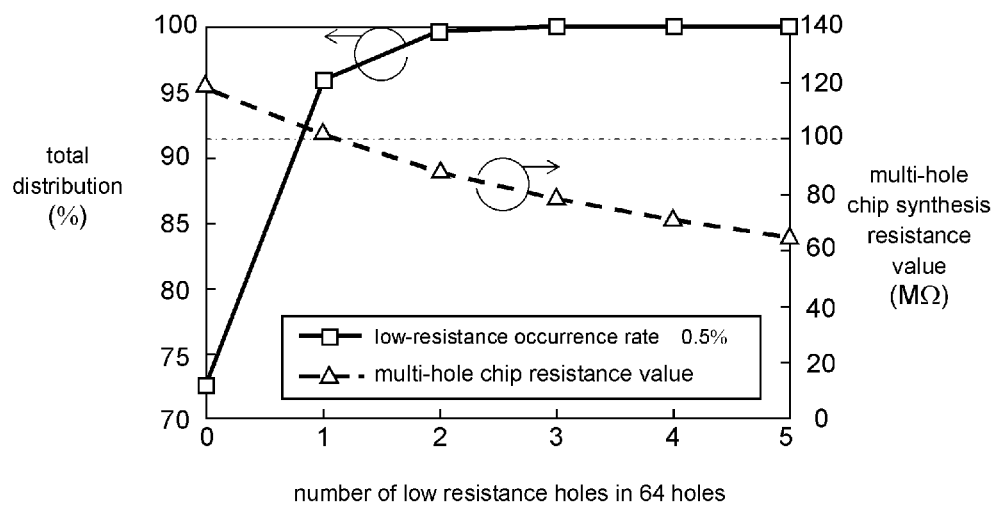
FIG. 13 is a graph showing binomial distribution and a combined resistance value of the multi-hole sensor chip in accordance with the exemplary embodiment of the present invention.

FIG. 12 is a graph showing distribution of seal resistance values of the single-hole sensor chip in accordance with the exemplary embodiment of the present invention. FIG. 13 is a graph showing binomial distribution and a combined resistance value of the multi-hole sensor chip in accordance with the exemplary embodiment of the present invention.

As shown in FIG. 12, distribution of resistance values of single-hole sensor chip 3011 shows so-called double peak, that is, has two distribution of high resistance of not less than 500 MΩ and low resistance of not more than 10 MΩ. That is to say, it can be said that a cell electrophysiological measurement device on which a plurality of single-hole sensor chips 3011 are mounted has high performance when the amount of low-resistance components is small and the ratio of the high-resistance components is high. However, several percents of the low-resistance components are generated as long as a surface state of gigaseal is to be obtained.

On the other hand, in multi-hole sensor chip 3012, since plurality of specimens 112 are captured by each of the plurality of through holes 309, variations of individual specimens 112 themselves can be averaged. Therefore, as compared with single-hole sensor chip 3011, uniform results in which variation among sensor chips 3012 is small can be obtained easily. The resistance values of multi-hole sensor chip 3012 is combined resistance value of individual resistance values of through holes 309 opened in diaphragm 306, the combined resistance value of multi-hole sensor chip 3012 in which N holes are opened in one chip is represented by the following mathematical formula Math. 1.

$$\frac{1}{R} = \frac{1}{R_1} + \frac{1}{R_2} + \frac{1}{R_3} + \ldots + \frac{1}{R_N} \quad \text{[Math. 1]}$$

Herein, R denotes a combined resistance value, $R_n$ (n=1, 2, ..., N) denotes individual resistance values. This is converted into an average resistance value Rave per one hole, a value represented by the following mathematical formula Math. 2.

$$R_{ave} = R \times N \quad \text{[Math. 2]}$$

Thus, even if a large number of through holes 309 of multi-hole sensor chip 3012 have a high resistance value such as a gigaseal, if small number of through holes 309 have a high resistance value of several MΩ, the combined resistance becomes a low resistance value.

Next, a calculation example of the combined resistance of multi-hole sensor chip 3012 having 64 through holes 309 is described.

In multi-hole sensor chip 3012, some leakage current is allowed. Ideally, however, it is preferable that each hole has a resistance value of 100 MΩ. When 64 through holes 309 are provided, a combined resistance value is calculated when a success resistance value that specimen 112 is captured by through holes 309 is 120 MΩ and a low resistance value that fails capturing and resistance is lowered is 10 MΩ, and the combined resistance value is converted into the resistance value per hole. As a result, as shown in FIG. 13, in order to secure the resistance value of 100 MΩ per hole, a low-resistance component that can be permitted to have 10 MΩ is not more than one hole among 64 holes. Furthermore, from the calculation of the binomial distribution, in order to secure a resistance value of not less than 100 MΩ at the rate of not lower than 95%, occurrence rate of low-resistance components having not more than 10 MΩ is required to be suppressed to about not more than 0.5%.

From these calculation results, it is shown that the chip surface of multi-hole sensor chip 3012 is required to be treated in a different state from that of the chip surfaces of single-hole sensor chip 3011 in which several % of low-resistance components are generated. That is to say, the surface hydrophilic property necessary for multi-hole sensor chip 3012 is not so strong adhesion but a moderate adhesion and a balance without generating low.

Next, measurement of the surface potential is described.

An electric field is applied to positively or negatively charged colloidal particles in a solution from the outside, the particles migrate in the direction opposite to the sign of electric charges. The migrating particles are irradiated with light, and the surface potential can be calculated from the Doppler shift amount that is proportional to the scattered light. For measuring the surface potential of a specimen, a zeta electric potential measurement device ELS-Z manufactured by Otsuka Electronics Co., Ltd. which is capable of measuring a plate-like specimen is used, but, for example, a zeta electric potential measurement device SurPASS manufactured by Anton Paar may be used.

The present inventors measure surface potential by subjecting of a TEG (Test Element Group) substrate of $SiO_2$ to the below-mentioned three types of surface treatment by using surface electrometer ELS-Z manufactured by Otsuka Electronics Co., Ltd. Furthermore, the compositions of surfaces of the TEG substrates to which the same treatment is carried out respectively are analyzed by using XPS.

In TEG sample 1, after oxide film 116 is formed by a thermal oxidation process in which a Si single crystal substrate is heated in an atmosphere of oxygen and water vapor at 1100° C., washed with an ammonium fluoride buffered hydrofluoric acid solution and then subjected to ashing treatment with oxygen plasma (oxygen ashing).

As TEG sample 2, a Si substrate is subjected to the same treatment as in sample 2 in the first exemplary embodiment. That is to say, in TEG sample 2, oxide film 116 is formed by thermal oxidation process in which heating is carried out at 1100° C. in an atmosphere of oxygen and water vapor, and then, an oxynitride film as noncrystalline solid layer 117 is formed by thermal nitridation by heating to 1100° C. in an atmosphere of ammonia.

In TEG sample 3, oxide film 116 is formed by thermal oxidation process in which a Si single crystal substrate is heated at 1100° C. in an atmosphere of oxygen and water vapor, then washed with an ammonium fluoride buffered hydrofluoric acid solution and dried.

As a result, the measurement results of the surface potential in each TEG sample are shown in Table 2.

TABLE 2

| Sample | Surface Potential (mV) |
|---|---|
| TEG sample 1 | −25.3 |
| TEG sample 2 | −11.8 |
| TEG sample 3 | +18.0 |

As shown in Table 2, the measured surface potential of TEG sample 3, in which a $SiO_2$ substrate has been washed, is +18.0 mV. As shown in comparative sample 2 in FIG. 5 of the first exemplary embodiment, when the $SiO_2$ substrate is subjected only to BHF washing, a gigaseal success rate is about more than 30%.

As shown in sample 1 in FIG. 5, when the $SiO_2$ substrate is subjected to BHF washing and then to ashing treatment with oxygen plasma, the gigaseal success rate exceeds 90%. A measurement value of the surface charge of TEG sample 1 is −25.3 mV. From these results, it is shown that the surface potential becomes positive when only BHF washing is carried out, and the surface potential becomes negative when BHF washing is carried out and then ashing treatment with oxygen plasma is carried out.

Furthermore, in sample 2, as compared with sample 1, the gigaseal success rate is somewhat lowered, and, at the same time, an absolute value of the surface potential is somewhat reduced. As discussed above, the results support the correlation of the affinity between the surface and a cell with respect to the surface potential.

Furthermore, when TEG sample 2 in which an oxynitride film is formed on the $SiO_2$ substrate is measured by XPS, the carbon amount is 9%. The rate of nitrogen is high as 27%, and Si:O:N≈1:1:1 is satisfied. The measurement result of the surface potential after the surface treatment is −11.8 mV.

These results show the following things.

Firstly, when only BHF washing is carried out as surface treatment of the $SiO_2$ substrate, the gigaseal success rate exceeds 30%, which exhibits higher performance than the case where the surface treatment is not carried out (FIG. 5). Furthermore, in this treatment, the surface potential of the substrate has positive charge, which is not suitable from the viewpoint of attachment of a specimen.

Next, as a surface treatment of the $SiO_2$ substrate, when ashing treatment with oxygen plasma is carried out after BHF washing, the gigaseal success rate exceeds 90%, which exhibits high performance when it is used as a single-hole sensor chip. Furthermore, the surface potential after this treatment is not more than −20 mV.

Furthermore, when an oxynitride film is formed on the $SiO_2$ substrate, Si:O:N≈1:1:1 is satisfied. The bonding energy between oxygen and nitrogen in Si.O.N is extremely strong, which can prevent the replacement to carbon that reduces a hydrophilic property. As a result, as shown in FIG. 8 in the first exemplary embodiment, deterioration over time is reduced. The gigaseal success rate is not so extremely high, but the adhesion is somewhat weakened for that. Then, cells move on the through hole relatively freely, and the low-resistance component is reduced. Therefore, it is suitable for the surface treatment with respect to multi-hole sensor chip 3012. The surface potential after the surface treatment is carried out is −11.8 mV. It is thought that not too strong negative charge provides adhesion suitable for a plurality of holes.

That is to say, it is suitable that single-hole sensor chip 3011 is subjected ashing treatment with oxygen plasma after BHF washing, and the surface charge is desirably not more than −20 mV. Furthermore, in multi-hole sensor chip 3012, thermal nitridation treatment in which an oxynitride film is formed on the $SiO_2$ substrate is optimum, and it is desirable that the surface charge is not less than −20 mV and less than 0 mV.

When treatment of TEG sample 2 is carried out, negative electric potential of sensor chip 3011, 3012 can be maintained even at ordinary temperature. Therefore, storage at ordinary temperature is possible.

As mentioned above, as the surface treatment method for the $SiO_2$ substrate, when ashing treatment with oxygen plasma is carried out after BHF washing, a silanol group (Si.OH) can be modified. In order to achieve the gigaseal state at high rate, it is necessary that a silanol group is bonded on the surface of the sensor chip, and the surface state is kept. However, as shown in FIG. 7, when the surface treated sensor chip is left at ordinary temperature, deterioration of the sensor chip proceeds after 5 hours.

This deterioration is caused because a Si.OH bond that is a weak bond on the surface of the sensor chip is changed to a stronger and more stable Si.C bond. Therefore, it is important that a cell electrophysiological measurement device after surface treatment is stored in an extreme freezing environment and does not cause a chemical reaction.

On the other hand, in general, since a Si.ON bond after thermal nitridation treatment is strong and stable, it is less possibility that replacement to carbon easily occurs at ordinary temperature as in a Si.OH bond, and a siloxane bond occurs by dehydration. This is because, as shown in FIG. 8, it is experimentally recognized that the gigaseal success rate is not deteriorated even after passage of two weeks after the thermal nitridation.

That is to say, since the negative electric potential on the surface of sensor chip 3011, 3012 can be maintained at ordinary temperature, storage of the cell electrophysiological measurement device does not require a freezer. Therefore, the cost necessary for storage can be reduced.

Furthermore, when the surface of sensor chip 3011, 3012 has negative electric potential, it is thought that the Si.OH bond is not replaced by the Si.C bond. Therefore, by using the surface potential of sensor chip 3011, 3012 for quality control, the quality control of a cell electrophysiological measurement device can be simply carried out without carrying out measurement of a cell as destructive inspection.

Furthermore, how a specimen as biological sample material such as a cell adheres to through hole 309 formed on single-hole sensor chip 3011 is observed by using an optical microscope. The results of observation are shown below. Herein, single-hole sensor chip 3011 is fixed on the bottom surface of a well.

Figure 14A:
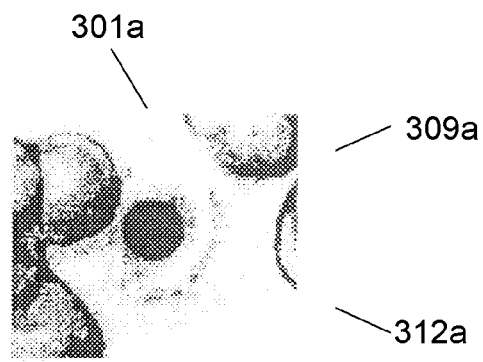
FIG. 14A is an electron microscope photograph of an upper surface of a through hole of a sensor chip in a gigaseal state in accordance with an exemplary embodiment of the present invention.
Figure 14B:
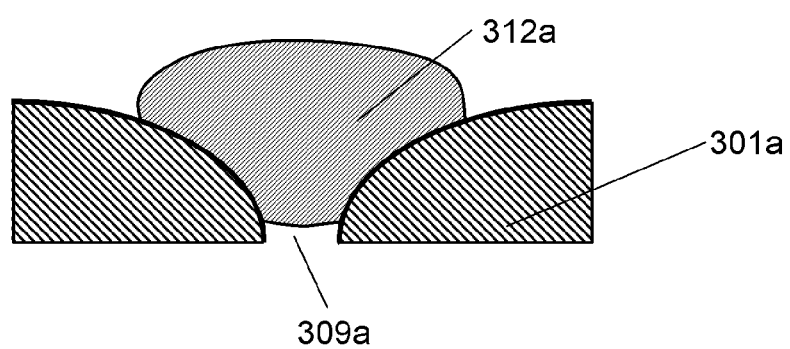
FIG. 14B is a sectional view of the through hole of the sensor chip in a gigaseal state in accordance with the exemplary embodiment of the present invention.
Figure 15A:
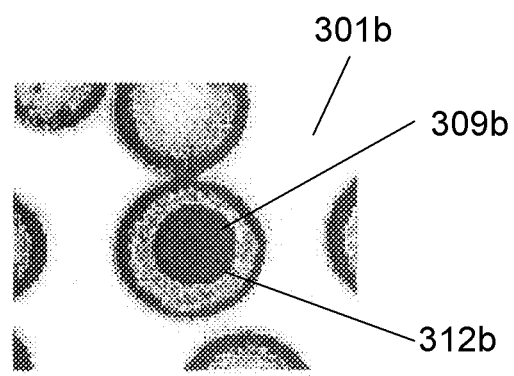
FIG. 15A is an electron microscope photograph of an upper surface of a through hole of a sensor chip not in a gigaseal state in accordance with an exemplary embodiment of the present invention.
Figure 15B:
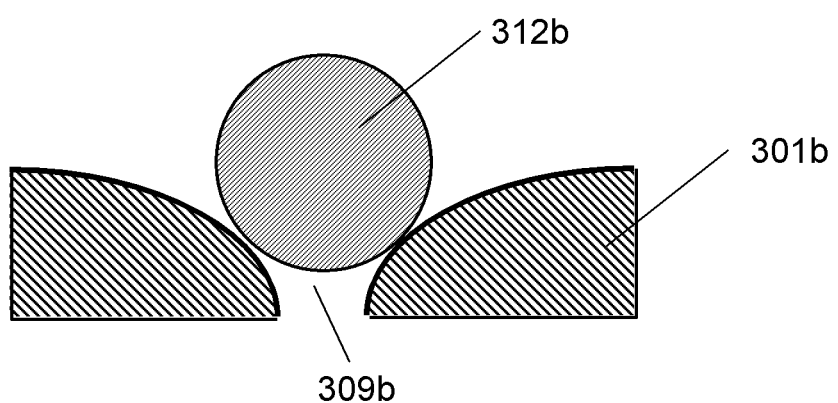
FIG. 15B is a sectional view of the through hole of the sensor chip not in a gigaseal state in accordance with the exemplary embodiment of the present invention.

FIGS. 14A and 15A are top views of electron microscope photographs taken by a cell electrophysiological measurement device. FIG. 14A is a top view of electron microscope photograph for illustrating sensor chip 301a in which a gigaseal is obtained. FIG. 15A is a top view of electron microscope photograph for illustrating sensor chip 301a which does not reach a gigaseal. FIGS. 14B and 15B show schematic sectional views, respectively. Samples shown in FIGS. 14A and 14B show a sealing property, that is, a high resistance seal of not less than 500 MΩ.

Thus, it is shown that there is a large difference in how specimen 312a attaches to through hole 309 between sensor chip 301a in which a gigaseal is obtained and sensor chip 301b in which a gigaseal is not obtained.

In sensor chip 301a in which a gigaseal is obtained, a cell as specimen 312a is attached to through hole 309a while it changes the shape and does not maintain a spherical shape.

On the other hand, in sensor chip 301b in which a gigaseal is not obtained, a cell as specimen 312b is brought into contact with through hole 309b without changing a spherical shape.

That is to say, in order to obtain a gigaseal, it is not sufficient that a specimen is brought into contact with the through hole, but the diaphragm surface of a sensor chip is required to have a surface state in which a specimen is deformed.

Figure 16:
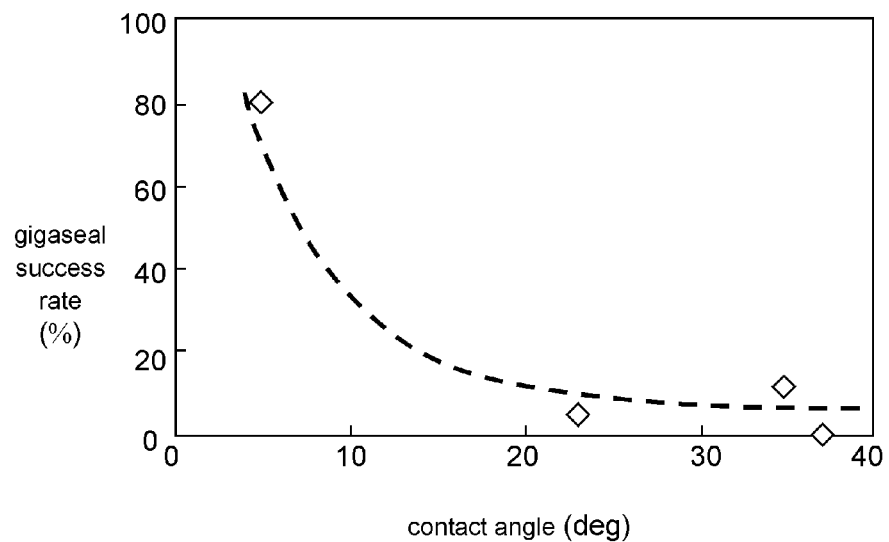
FIG. 16 is a graph showing a relation between a contact angle of water and the gigaseal success rate in the sensor chip in accordance with the exemplary embodiment of the present invention.

In this way, it is expected that the adhesion of a specimen depends upon the hydrophilic property of the surface of the diaphragm of the sensor chip. Herein, a contact angle of each of sensor chips 301a and 301b with respect to a first surface of water is measured. FIG. 16 shows a relation between a contact angle of sensor chips 301a and 301b with respect to water and a gigaseal success rate. In a cell electrophysiological measurement device on which a sensor chip having a small contact angle, that is, having a high hydrophilic property is mounted, a high gigaseal success rate is shown. On the other hand, in a cell electrophysiological measurement device on which a sensor chip having a large contact angle, that is, a high hydrophilic property is mounted, a low gigaseal success rate is shown. The sensor chip having a large contact angle has a hydrophobic substance attached on the diaphragm surface thereof.

An effect of improvement of affinity between the surface of the sensor chip and a specimen by enhancing the hydrophilic property of the surface of the sensor chip can be described as follows from the viewpoint of the surface potential of the diaphragm.

When a cell is used as a specimen, when the structure of the cell membrane is considered, a hydrophilic part existing outside of a phospholipid double membrane structure has a structure in which alcohols having a polarity, for example, choline, ethanol amine, serine, and inositol are bonded to the outer side of phosphoric acid by an ester bond. Since this phosphoric acid ester site has a polarity, the cell membrane shows a hydrophilic property. When the structure of phosphoric acid ester is found minutely, charge as a whole of negatively charged phosphoric acid and alcohol is negative.

However, when interaction between cells dispersed in PBS (phosphate buffered saline) and silicon oxide on the surface of the diaphragm is taken into consideration, it is necessary to consider the shielding effect of electric charge by an electrolyte in PBS. The distance between a phosphoric acid in a phosphate ester structure and the charged center of alcohol is about 5 to 10 Angstrom. On the other hand, a shielding distance (Debye length) in electric charges in PBS is about 8 to 12 Angstrom. Therefore, when the cell is seen from the outside of the cell membrane, a negative charge of phosphoric acid cannot be seen because it is shielded, and only positive charges of alcohol such as choline and ethanol amine can be seen. Therefore, when the diaphragm has negative surface potential, it attracts positive charges on the outermost surface of the cell membrane to each other. Thus, high affinity is shown. Furthermore, a diaphragm having negative surface potential shows a hydrophilic property. As compared with the results of FIG. 5, as the negative surface potential is increased, a gigaseal success rate becomes higher. That is to say, the results support the correlation between the affinity of the surface with respect to a cell and the surface potential.

Next, for identification of a substance providing a surface of diaphragm 306 of sensor chip 3011, 3012 with a hydrophobic property, measurement using XPS is carried out. Surface treatment states of the measured $SiO_2$ substrate are shown in Table 3.

As sample 5, diaphragm 306 is subjected to BHF washing and then ashing treatment, and stored in a nitrogen desiccator for two weeks.

As sample 6, diaphragm 306 is subjected to BHF washing and then ashing treatment, and stored in frozen state at −40° C.

As comparative sample 3, a $SiO_2$ substrate that has not been subjected to surface treatment is used.

TABLE 3

| | C | N | O | F | Na | Mg | Si | Ca | Fe | Ba (atom %) |
|---|---|---|---|---|---|---|---|---|---|---|
| Comparative sample 3 | 4.5 | 0.2 | 66.2 | 0.1 | 0.1 | 0.0 | 28.8 | 0.0 | 0.1 | 0.0 |
| Sample 5 | 4.2 | 0.2 | 66.8 | 0.1 | 0.0 | 0.0 | 28.6 | 0.0 | 0.0 | 0.0 |
| Sample 6 | 0.8 | 0.0 | 69.6 | 0.1 | 0.0 | 0.0 | 29.4 | 0.0 | 0.0 | 0.0 |

As shown in Table 3, other than Si and O as a main component of the $SiO_2$ substrate, much C (hereinafter, referred to as carbon) are observed. It is determined that the carbon is hydrophobic substance that reduces an adhesion force between a specimen and a sensor chip. The correlation between the amount of a carbon and a gigaseal success rate is examined.

Figure 17:
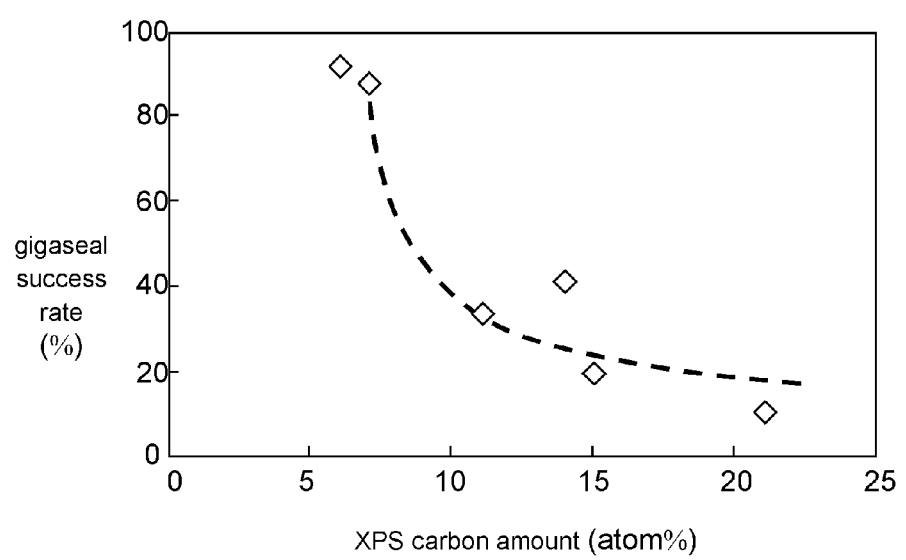
FIG. 17 is a graph showing a relation between a carbon amount by XPS and the gigaseal success rate in the sensor chip in accordance with the exemplary embodiment of the present invention.
Figure 18:
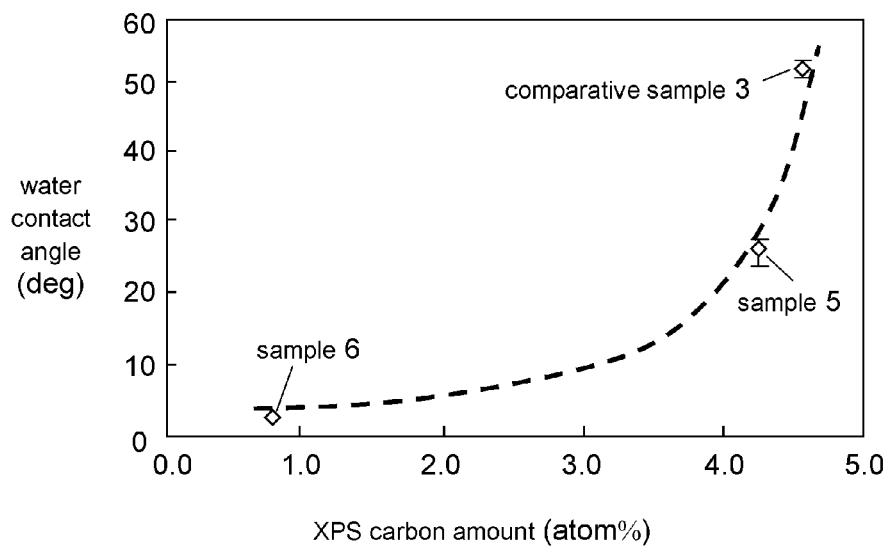
FIG. 18 is a graph showing a relation between a contact angle of water and a carbon amount by XPS in the sensor chip in accordance with the exemplary embodiment of the present invention.

As a result, as shown in FIG. 17, when the carbon amount is increased, the gigaseal success rate is lowered. Furthermore, a contact angle of water is measured. FIG. 18 shows correlation between a carbon amount obtained from the XPS results and the contact angle of water. A substrate having a large carbon amount has a large contact angle, and a substrate having a small carbon amount has a small contact angle. That is to say, it can be determined that the cause for enhancing the hydrophobic property is carbon on the substrate surface.

From the series of examination, it is shown that carbon on the substrate surface give a large effect on the adhesion between the specimen and the sensor chip, that is, the gigaseal success rate. As is apparent from the experiment results, if the carbon amount is not more than about 10%, the specimen and the sensor chip show high adhesion.

Carbon attached on the surface of the sensor chip includes volatile components of adhesive agents used for allowing the sensor chip to adhere to the well in addition to carbon contained in the air. These carbon components can be detected by GC-MS (Gas Chromatograph-Mass Spectrometry).

As mentioned above, carbon attached on the sensor chip can be removed by BHF washing. Furthermore, after the BHF washing is carried out, ashing treatment with oxygen plasma is carried out, ability for removing carbon on the surface of the sensor chip can be enhanced. That is to say, as shown in FIG. 5, comparative sample 1 that has not been subjected to BHF washing shows a low gigaseal success rate of ten and several %. Comparative sample 2 that has been subjected to BHF washing shows a gigaseal success rate of more than 30%. Sample 1 that has been subjected to BHF washing and then ashing treatment with oxygen plasma shows a gigaseal success rate of more than 90%.

However, when surface treatment shown in sample 1 is carried out, the gigaseal success rate is lowered with the passage of time after treatment as shown in FIG. 7. This is expected that hydrophobic carbon or carbon compounds are attached again on the surface of the sensor chip which is activated and whose hydrophilic property is enhanced, so that the surface hydrophilic property of the sensor chip is lowered. Therefore, after carbon on the surface of the sensor chip is removed, as mentioned above, it is effective to form a method for forming a noncrystalline solid layer having a hydrophilic property and high binding energy on the $SiO_2$ substrate. As these noncrystalline solid layers, in the sensor chip on which an oxynitride film is formed, as shown in FIG. 8, deterioration after long-time storage is not observed. That is to say, by forming an oxynitride film, attachment of carbon can be reduced.

Fourth Exemplary Embodiment

Hereinafter, a cell electrophysiological measurement device of a fourth exemplary embodiment of the present invention is described with reference to drawings.

As shown in FIG. 3, noncrystalline solid layer 117 formed on at least one surface of first surface 110 and second surface 111 of diaphragm 106 has distribution in which the composition ratio in terms of the number of atoms of nitrogen is exponentially reduced from the outermost surface to the thickness of about 10 nm without having an inflection point. Furthermore, in FIGS. 11A and 11B, the surface potential of at least one of first surface 310 and second surface 311 of diaphragm 306 is negative electric potential. The electric potential is increased not uniformly but gradually in the thickness direction from the surface to the center of the negative electric potential. The electric potential inside of diaphragm 306 in FIGS. 11A and 11B is different from the electric potential of at least one surface of first surface 310 or second surface 311. The electric potential shows distribution that is reduced from the inside of diaphragm 306 toward first surface 310 or second surface 311.

Note here that the electric potential inside diaphragm 306 in this exemplary embodiment means a virtual surface potential obtained when it is assumed that a virtual surface having a certain depth from the surface to the inside of diaphragm 306 is present and the surface appears on the outermost surface by operation such as etching.

In this exemplary embodiment, by using this property, the adhesion between specimen 112 and sensor chip 101 is controlled more efficiently. That is to say, the polarizability in a unit lattice differs from the outermost surface to the center of the sensor chip, and the density of nitrogen in noncrystalline solid layer 117 is gradually reduced. Alternatively, the electric potential of diaphragm 306 is gradually increased from the outermost surface to the center in the thickness. From these things, in accordance with the objectives for measurement, the surface state can be changed to the optimal state for measurement easily.

For example, when specimen 112 is allowed to adhere to single-hole sensor chip 3011 strongly, an oxynitride film only needs to be etched so as to expose a $SiO_2$ film, and then subjected to BHF washing and oxygen plasma treatment. On the other hand, as in multi-hole sensor chip 3012, when the adhesion between specimen 112 and multi-hole sensor chip 3012 may not be high and a low-resistance component of not higher than 10 MΩ is not desired to appear, an oxynitride film may be used as it is without etching. A combined resistance value obtained by the number of through holes 109 existing in one sensor chip or the number of low-resistance components permitted thereby are different. Therefore, according to the number of holes and necessary resistance values, the etching amount of the oxynitride film may be determined. This control is possible because the oxynitride film has a feature of not being uniform in the thickness direction. Furthermore, as mentioned above, since the resistance value distribution and the surface potential correlate to each other, it is possible to know approximate resistance value distribution by measuring the surface potential of the oxynitride film after etching. Therefore, in quality control, a test can be carried out without destroying a product.

Other methods for forming an oxynitride film include a CVD method, a sputtering method, a CSD method, plasma nitridation, thermal nitridation, and the like. An arbitrary method among them may be selected. Thermal nitridation is particularly desirable. By carrying out thermal nitridation, the oxynitride film is formed also on the inner wall of through hole 109 in a uniform film thickness. Specimen 112 is attached to not only diaphragm 306 but also a side wall of through hole 109 by a negative pressure. Therefore, when the oxynitride film is formed on the side wall of through hole 109 in a uniform film thickness, a state having higher adhesion is obtained.

When the CVD method, the sputtering method, the CSD method, and the like, are selected, it is difficult to apply an oxynitride film uniformly. Since the oxynitride film is not formed on the inner wall of through hole 109 (in particular, deep portion), an effect of improving the adhesion by the oxynitride film is reduced. In plasma nitridation, plasma having directivity is generated by using a bias voltage, it is difficult to carry out uniform application similar to the CVD method. When plasma without having directivity is used, the same effect as in the thermal nitridation is obtained, but productivity of devices, production cost, and the like, are taken into consideration, thermal nitridation is excellent.

In the thermal nitridation, it is desirable that an entire chip is heated in an atmosphere containing, for example, a reducing gas such as $NH_3$. The reducing gas refers to as an atmosphere including gases such as $H_2$, $CO$, $H_2S$, $SO_2$, and HCHO (formaldehyde) in addition to $NH_3$. An atmosphere appropriately containing $N_2$ in addition to these gases is more preferable.

By carrying out thermal nitridation, an oxynitride film is formed also on the rear surface of diaphragm 306 (that is, second surface 111) or on the periphery of sensor chip 101.

When the CVD method, the sputtering method, the CSD method, and the like, are selected, it is difficult to apply an oxynitride film also on the rear surface of diaphragm 306. Therefore, due to the stress of the oxynitride film, warp or cracking may occur in diaphragm 306, or the oxynitride film may be peeled off. By carrying out thermal nitridation, the oxynitride film is formed also on the rear surface of diaphragm 306 or in the periphery of sensor chip 101. Therefore, since the stress is applied to diaphragm 306 uniformly, warp or cracking does not occur and the oxynitride film is not peeled off, which provides excellent productivity.

Furthermore, since the oxynitride film formed by thermal nitridation has gradient distribution, it has excellent adhesion with respect to sensor chip 3011, 3012. The difference in electronegativity with respect to silicon between oxygen and nitrogen determines the surface potential. Since the electronegativity of nitrogen is lower, the density of nitrogen becomes higher, thus reducing the bias of electric charge. As a result, an absolute value of the surface potential is reduced when it appears on the surface of diaphragm 306. A pure nitridation film has strong stress, and the oxynitride film generates stress according to the composition. Therefore, on the surface of the sensor chip 3011, 3012 made of silicon, peeling easily occurs. Due to gradient distribution, the stress is gradually relieved, and therefore the peeling easily occurs.

Entire sensor chip 3011, 3012 is uniformly oxynitrided, and when it has gradient distribution in the depth (thickness) direction, it is shown to be thermally nitrided. The composition of the oxynitride film can be arbitrarily controlled by temperatures, times, atmosphere, and gradient distribution.

Fifth Exemplary Embodiment

Hereinafter, a sensor chip in accordance with this exemplary embodiment is described. Note here that the same reference numerals are given to the same configurations as in the preceding exemplary embodiments and detailed description thereof is omitted. The present invention is not necessarily limited to the following exemplary embodiment. This exemplary embodiment is different from the first exemplary embodiment in that a sensor chip is made of a nanofiber plate.

Figure 19:
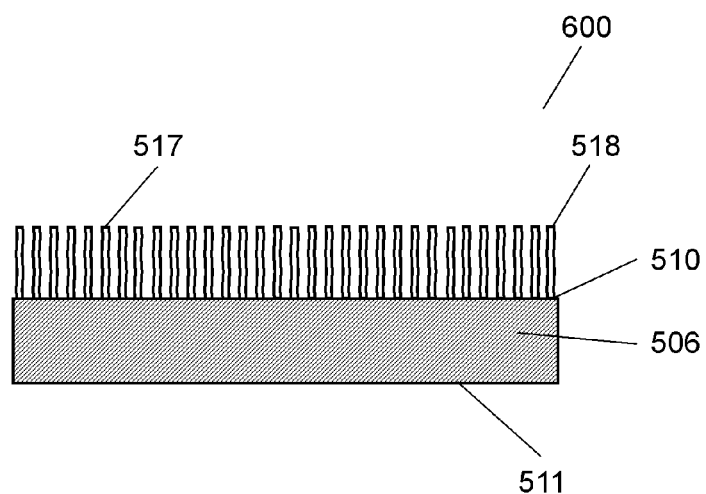
FIG. 19 is a sectional view of another sensor chip in accordance with an exemplary embodiment of the present invention.

FIG. 19 is a sectional view showing a sensor chip in this exemplary embodiment. Sensor chip 600 measures a property of a substance by adsorbing biological tissue, a cell, protein, nucleic acid, peptide, a sugar chain, a virus, and the like, on the surface of nanofiber 518.

Sensor chip 600 includes diaphragm 506, and a plurality of nanofibers 518 joined to first surface 510 of diaphragm 506. Diaphragm 506 includes first surface 510 and second surface 511 spatially separated from first surface 510. Nanofiber 518 includes silicon oxide or preferably silicon dioxide having a nanoscale diameter, and has an OH group on a part of the surface thereof. The surface of nanofiber 518 is covered with noncrystalline solid layer 517 containing SiOX as a main component, and substance X includes an element having a higher electronegativity than that of silicon.

When the surface of the nanofiber adsorbs a substance such as protein, nucleic acid, peptide, a sugar chain, a virus, or the like, it is possible to detect whether or not a test subject includes a predetermined substance.

In this way, since the surface of nanofiber 518 is covered with noncrystalline solid layer 517, dissociation of an OH group formed on the surface is suppressed. As a result, the stability of the surface of nanofiber 518 is achieved. This exhibits an effect in preventing dissociation of the OH group after the OH group is formed on a part of the surface and before measurement is carried out in manufacture of the sensor chip.

Furthermore, even when, for example, a silane coupling agent is reacted on the upper layer of noncrystalline solid layer 517, they can be formed similarly stably.

The sensor chip of this exemplary embodiment can be used for a DNA array, a protein array, a sugar chain array, a micro fluid chip, and a cell culture chip.

Note here that a nanofiber plate in this exemplary embodiment can be used as an array substrate. An array substrate is a substrate capable of carrying out an analysis by allowing the interaction between a detection substance and a target substance contained in a test material to progress, and detecting the degree of interaction by fluorescence intensity, or the like. By providing a reaction field region that is a field previously causing the interaction on the substrate surface in an array, fixing a detection substance that is a target of each reaction field region, respectively, and then dropping a solution as a test material, a test material is analyzed. With such a configuration, a plurality of measurement can be carried out with one plate. In order to make an array by arranging a plurality of reaction field regions on the nanofiber plate in this exemplary embodiment, usual means that are carried out with respect to a glass plate, and examples of the means include an ink jet dispenser, photolithography, a pin spot, and the like.

Sixth Exemplary Embodiment

Hereinafter, a storage method of a sensor chip in accordance with this exemplary embodiment is described. Note here that the same reference numerals are given to the same configurations as in the preceding exemplary embodiments and detailed description thereof is omitted. Furthermore, the present invention is not necessarily limited to the following exemplary embodiment.

The sensor chip in this exemplary embodiment is a sensor chip shown in the first to fourth exemplary embodiments, and measuring a property of a substance by adsorbing biological tissue, a cell, protein, nucleic acid, peptide, a sugar chain, a virus, or the like, on the surface thereof. The sensor chip includes a diaphragm including a first surface, a second surface spatially separated from the first surface, and at least one through hole penetrating form the first surface to the second surface of the diaphragm. The property of such a substance can be measured by adsorbing biological tissue, a cell, protein, nucleic acid, peptide, a sugar chain, a virus, and the like, on the through holes formed on the sensor chip. The diaphragm can be formed of at least inorganic materials such as glass, silicon, silicon oxide, thermal oxidation $SiO_2$, polysilicon, amorphous silicon or a mixture thereof. Alternatively, the sensor chip may be a sensor device to which resin materials such as polydimethyl siloxane (PDMS), polypropylene, polycarbonate, polyolefin, polyethylene, polystyrene, polyamide, polymethylmethacrylate (PMMA), and cyclic polyolefin are joined.

Such a sensor chip or a sensor device is enclosed in at least a tightly closed package and sealed, and then stored at temperatures lower than room temperature (25° C.). The package is formed of resin such as aluminum or polydimethyl siloxane (PDMS), polypropylene, polycarbonate, polyolefin, polyethylene, polystyrene, polyamide, polymethylmethacrylate (PMMA), and cyclic polyolefin.

Herein, the temperatures lower than room temperature are at least not higher than 10° C., desirably not higher than 4° C., and more desirably below a freezing point. The storage at temperatures below the freezing point is desirably storage in a low-temperature environment of not higher than −10° C.

At this time, the atmosphere in the tightly closed package preferably includes gases such as helium, nitrogen, argon, krypton, and sulfur hexafluoride, which are usually inactive in an environment at not higher than room temperature.

The sensor chip is stored by the above-mentioned storage methods immediately before the use, and the sensor chip is returned to room temperature (25° C.) and immediately measured.

When the sensor chip is stored in this way, deterioration of property even after a long-time storage can be suppressed, and therefore, it is possible to provide a sensor chip capable of being stored for a long time.

The following is description of an effect that the sensor chip or the sensor device is enclosed in at least a tightly closed package and sealed, and stored at temperatures lower than room temperature.

When the sensor chip or the sensor device is stored at temperatures lower than room temperature, attachment of adsorption inhibition substances is reduced. The adsorption inhibition substances inhibits the adsorption of adsorption substances on a region in which the adsorption substances such as biological tissue, a cell, protein, nucleic acid, peptide, a sugar chain, a virus, are adsorbed, for example, in the periphery of the through hole of the sensor chip. In general, in many cases, such an adsorption inhibiting substance is, for example, an organic compound that volatilizes from resin materials or adhesive agents which are used for the package, the sensor chip or the sensor device, or small amount of organic compounds existing in the atmosphere. In the storage state before measurement of inputting substances such as a cell, when an adsorption inhibiting substance is adsorbed on the surface of the sensor chip, a substance as a subject to be measured is not easily adsorbed, and measurement accuracy is lowered. That is to say, in a conventional cell electrophysiological measurement device as one example of a sensor device using a sensor chip, cell adsorption inhibiting substances are present on the surface of the through hole to which cells are adsorbed, and, thereby, cell adsorption to the through hole may not be sufficiently carried out. Therefore, a leakage current is generated between the cell surface and the through hole surface, which makes it difficult to improve the measurement accuracy. Therefore, as means for preventing adsorption of cell adsorption inhibiting substances to the surface of through holes, underwater storage for storing a sensor device immediately before the cells are adsorbed, vacuum storage for storing a sensor device in a vacuum chamber, are carried out. However, the underwater storage requires an operation for pulling out water from a sensor before measurement, and the vacuum storage may be insufficient in a storage effect.

However, when the sensor chip is stored at low temperatures as in this exemplary embodiment, volatilization of organic compounds is extremely reduced. Furthermore, even if an organic compound is present in the atmosphere, its kinetic energy is lowered due to low temperatures, and therefore it is not easily bonded or attached to the molecule. Therefore, unnecessary adsorption inhibiting substances are not easily attached on the surface of the through hole of the sensor chip. Furthermore, unlike conventionally used underwater storage, after a package is opened, water attached on the surface is not required to be pulled out before use, which leads to shortening of the time before operation.

A mechanism for stably maintaining the hydrophilic property as another effect is described. In the case like sample A in Table 1 in the first exemplary embodiment which includes only $SiO_2$, as already described, a change of a state between sample A and sample B in Table 1 occur reversibly on the outermost surface as in the chemical formula Chem. 1.

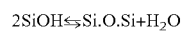  [Chem. 1]

It is known that the change of the state reaches equilibrium depending upon temperatures. At room temperature, the number of OH groups is estimated to be 5.6 to 5.9. That is to say, even if the number of OH groups on the outermost surface is 7.9 groups/nm$^2$ at maximum immediately after a sensor chip is manufactured, when it is left at room temperature regardless of whether the environment is water, vacuum, or an inert gas, dissociation of OH groups occurs and the number of OH groups is reduced from 7.9 groups/nm$^2$. This shows that it is difficult to store the sensor chip provided with OH groups on the outermost surface for a long time at room temperature.

In order to dissolve this problem, in this exemplary embodiment, the sensor chip is stored at temperatures lower than room temperature.

Table 4 shows change of a lifetime at each temperature in which the time at which a predetermined adhesion cannot be secured is defined as a lifetime and adhesion of a cell is an index in a cell electrophysiological measurement device as one example of the sensor device.

The lifetime that is 11.3 hours at room temperature (25° C.) is increased to 67 hours at 10° C. that is lower than room temperature and rapidly increased to 2058.8 hours at −15° C.

TABLE 4

| | Temperature (° C.) | | | | | | |
|---|---|---|---|---|---|---|---|
| | −80 | −20 | −15 | 4 | 10 | 25 | 37 |
| Expected lifetime (hour) | 963665869.1 | 4429.4 | 2058.8 | 144.1 | 67.0 | 11.3 | 3.1 |
| Expected lifetime (day) | 40152744.5 | 184.6 | 85.8 | 6.0 | 2.8 | 0.5 | 0.1 |
| Expected lifetime (year) | 110007.5 | 0.5 | 0.2 | 0.0 | 0.0 | 0.0 | 0.0 |

The reason why the lifetime is increased at temperatures lower than room temperature is why OH groups on the outermost layer are stable when the sensor chip is produced, resulting in keeping a state in which a hydrophilic property is high. That is to say, the lower the temperature becomes, the less the dissociation of OH groups becomes, and a high density of the OH groups at the time when the sensor chip is manufactured is maintained.

Note here that as a structure for keeping the hydrophilic property of the sensor chip, at least an outermost layer is made to have a SiOX structure in the first to fourth exemplary embodiments. That is to say, among the Si bonding arms of the outermost layer, by bonding NH$_2$ with at least one or more of the bonding arms, a more stable surface can be obtained. As mentioned above, when the outermost layer includes only OH groups, adjacent OH groups meet together, and thus dissociation into H$_2$O is generated. However, some bonding arms are terminated at a NH$_2$ group, the possibility at which OH groups are adjacent to each other is reduced. As a result, dissociation of OH groups is reduced. Furthermore, since the NH$_2$ group has the hydrophilic property similar to the OH group, the hydrophilic state of the sensor chip can be kept in a more stable state.

Herein, it is preferable that the inside of the package is not in a vacuum state. With this exemplary embodiment, adsorption inhibiting substance can be more suppressed as compared with the case where a vacuum storage is used. In vacuum storage, although organic compounds originally presenting in the atmosphere can be removed, the amount of organic compounds generated from resins or adhesive agents cannot be reduced. Furthermore, due to a vacuum, in the organic compounds volatilizing from resin or adhesive agents, an average free path is increased under vacuum and the kinetic energy is enhanced, and therefore bonding or attachment to the molecules that are present on the surface is promoted.

Furthermore, as mentioned above, in order to allow, for example, a cell to be adsorbed strongly on the surface formed of silicon dioxide (SiO$_2$), the amount of OH groups (hydroxy groups) bonded to a Si atom is necessary to be sufficient, and it is preferable that the amount of the OH groups is larger. However, the OH groups on the surface react with the adjacent OH groups, and phenomenon in which H$_2$O is dissociated from the surface occurs, and reaches an equilibrium state depending upon environment temperature conditions. At this time, as the environment temperature is higher, dissociation of OH proceeds, and at room temperature, the number of the OH groups on 1 nm$^2$ of the surface of amorphous silicon dioxide is 4.6 to 4.9. That is to say, at room temperature, regardless of whether a package environment is vacuum or an inert gas, dissociation of SiOH from the surface is not avoided to some extent.

Thus, it is more preferable that water vapor is filled inside of the package. When a H$_2$O gas is included in a package atmosphere, it is possible to prevent dissociation of OH from the surface. That is to say, the reaction represented by the chemical formula Chem. 1 occurs reversibly. In other words, when a H2O gas is included, an equilibrium state at each temperature can be shifted to the SiOH side (left side of the chemical formula Chem. 1). That is to say, the hydrophilic property is not easily lost. Due to the sensor chip storage method in this exemplary embodiment, the sensor chip can be used without dropping of measurement accuracy when it is used.

Figure 20:
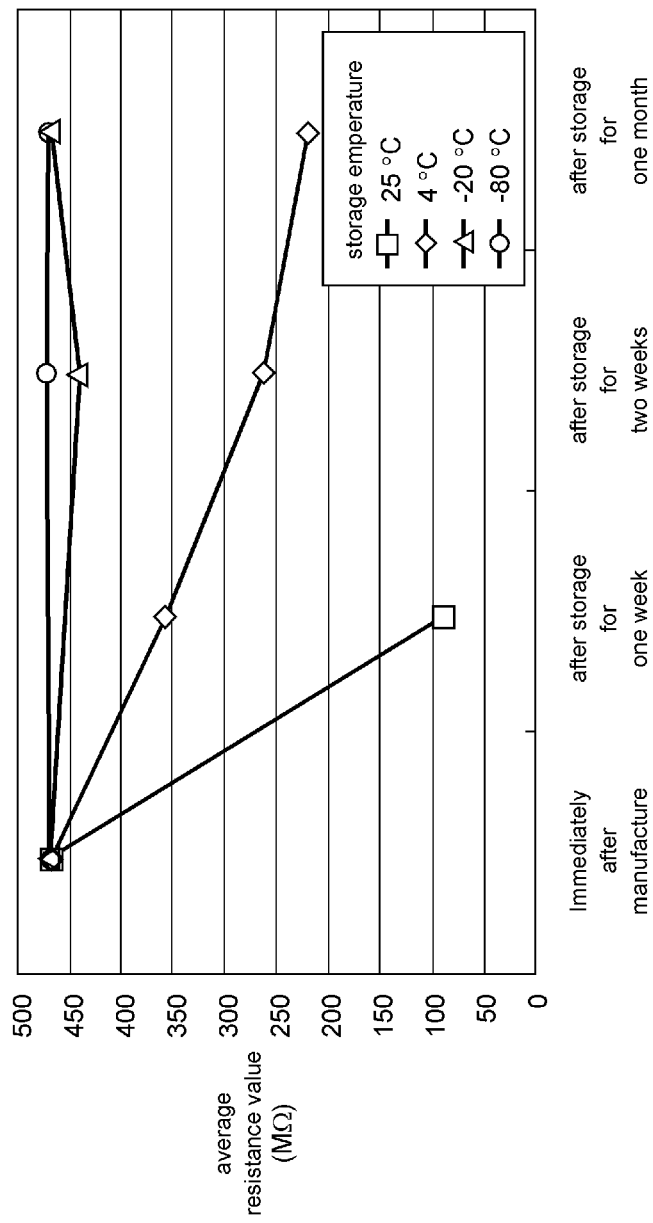
FIG. 20 is a graph showing a change over time of an average resistance value of the sensor chip in accordance with the exemplary embodiment of the present invention.

FIG. 20 is a graph showing time courses of average resistance values of the sensor chip in accordance with the exemplary embodiment of the present invention. As a sample, sensor chip 2012 shown in FIG. 9 or sensor chip 3012 shown in FIG. 11B is used, and a plurality of through holes are allowed to capture a cell.

Then, the same treatment is provided as in sample 3 in the second exemplary embodiment. That is to say, oxide film 116 is formed by a thermal oxidation process in which heating is carried out at 1100° C. in the atmosphere of oxygen and water vapor, and then washing with an ammonium fluoride buffered hydrofluoric acid solution is carried out. Furthermore, ashing treatment with oxygen plasma (oxygen ashing) is carried out.

Sensor chips are stored at room temperature (25° C.), 4° C., −20° C., and −80° C., respectively, and average values are measured after storage for one week, two weeks, and one month. Herein, a high average resistance value means a high capturing rate of a cell and means that an adsorption inhibiting substance is not easily attached.

When the sensor chip is stored at room temperature, the average resistance value is reduced. On the other hand, as compared with storage at room temperature, the average resistance value is not reduced in storage at 4° C., −20° C., and −80° C. even when the storing time becomes longer. In particular, this effect is remarkable when the sensor chip is stored at −20° C. and −80° C. Even in storage of longer than one month, the average resistance value is not different from that immediately after manufacture.

In other words, in storage at 4° C., −20° C., and −80° C., even when the storage time is longer, an adsorption inhibiting substance is not easily attached to the sensor chip. As a result, the capturing rate of a cell can be enhanced.

Note here that this exemplary embodiment describes a storage method of a sensor chip formed on a diaphragm and having a through hole. However, the sensor chip does not necessarily have a through hole, and may be a sensor chip having an adsorption surface on the surface. In this case, by the same storage method, deterioration of the property can be suppressed even in storage for a long time. Thus, it is possible to provide a highly precise sensor chip capable of being stored for a long time.

Seventh Exemplary Embodiment

Hereinafter, a storage method of a sensor chip in accordance with this exemplary embodiment is described. This exemplary embodiment is different from the sixth exemplary embodiment in that a sensor chip includes a nanofiber plate as shown in FIG. 19.

The sensor chip in this exemplary embodiment is a nanofiber plate provided with a substrate including silicon oxide or preferably, silicon dioxide having a nanoscale diameter. A cell, protein, nucleic acid, peptide, a sugar chain, a virus, or the like, is allowed to be adsorbed on the surface of the nanofiber, thereby detecting whether or not a specific substance is included in a subject to be tested.

In such a sensor chip, when an adsorption inhibiting substance for inhibiting adsorption of a substance as a target is adsorbed on the surface of the nanofiber before measurement is started, or a substance for inhibiting optical detection, for example, organic substances such as a $CH_3$ group and a COOH group from being adsorbed on the surface, the sensitivity of the sensor chip is remarkably inhibited. Therefore, a storage method is necessary for preventing adsorption of these inhibition substances after the sensor chip is manufactured.

Figure 21:
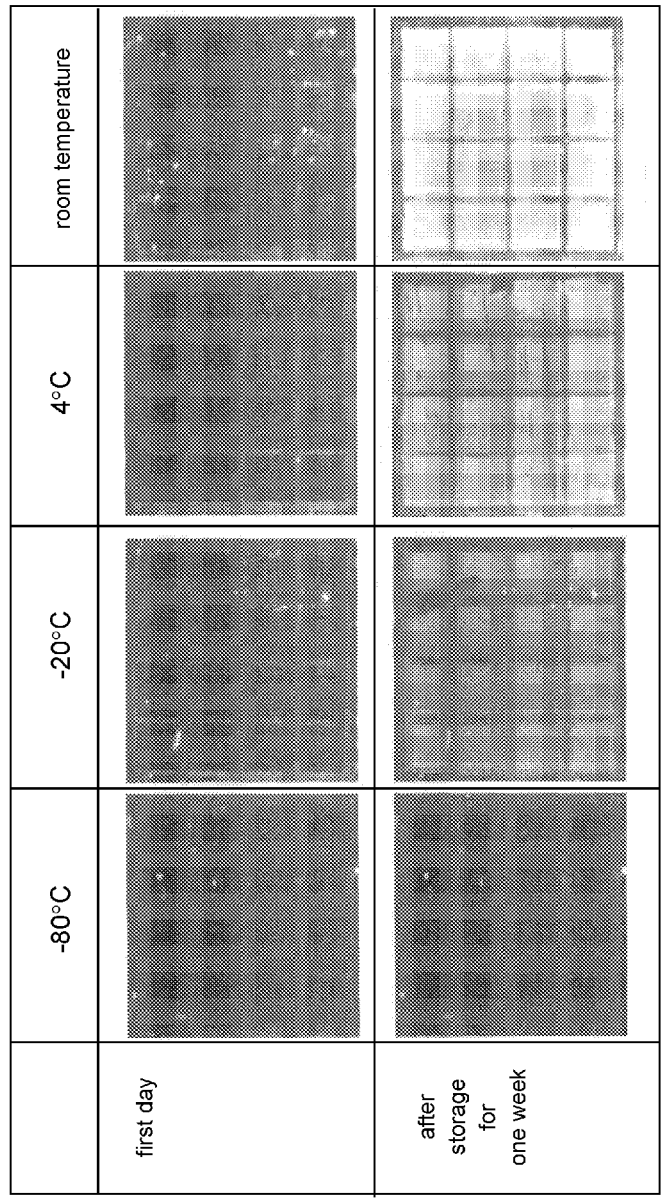
FIG. 21 shows observation results of the sensor chip in accordance with the exemplary embodiment of the present invention.

The above-mentioned sensor chip is observed immediately after it is manufactured, and after it is stored at room temperature (25° C.), or at low temperatures (4° C., −20° C., and −80° C.) for one week. FIG. 21 shows observation results of the sensor chip in accordance with the exemplary embodiment of the present invention. FIG. 21 shows an observation result of a sensor chip, in which the sensor chip is irradiated with laser (635 nm and 532 nm) by using a fluorescence plate reader (GenePix4000A) and a fluorescence state is photographed. Since a large number of adsorption inhibiting substances such as organic substances which inhibit an optical detection are attached on the sensor chip, optical back-ground noise is increased. That is to say, when the sensor chip emits light strongly, optical background noise is increased, which deteriorates the sensitivity of the sensor chip remarkably.

From FIG. 21, when a sensor chip is stored at room temperature, luminescence intensity of the sensor chip is increased. This is because a large number of adsorption inhibiting substances such as organic substances for inhibiting optical detection are attached on the sensor chip in storage at room temperature, and thus optical background noise is increased.

On the other hand, as compared with in storage at room temperature, in storage at temperatures lower than room temperature, for example, at 4° C., −20° C., and −80° C., the background noise is suppressed. That is to say, it is shown that in low-temperature storage, an adsorption inhibiting substance is not easily adsorbed on the sensor chip. In particular, this effect is remarkable when storage is carried out at −20° C. and −80° C., and optical background noise is not increased. Therefore, in storage at temperatures lower than room temperature, the optical background noise is suppressed. As a result, the sensitivity of the sensor chip can be maintained. As the storage temperature is lower than room temperature, this effect can be more remarkably achieved.

Note here that the surface of the nanofiber is covered with a noncrystalline solid layer containing SiOX as a main component, and substance X may include an element whose electronegativity is higher than that of silicon. When the surface of the nanofiber is covered with the noncrystalline solid layer, dissociation of the OH groups formed on the surface is suppressed, thus making the surface of the nanofiber stable. Thus, in manufacture of the sensor chip, dissociation of the OH groups can be prevented after the OH groups are configured on a part of the surface.

Furthermore, when a silane coupling agent is reacted to the upper layer of noncrystalline solid layer 517, it is possible to react the silane coupling agent stably.

The sensor chip of this exemplary embodiment can be used for a DNA array, a protein array, a sugar chain array, a micro fluid chip, and a cell culture chip. The nanofiber plate in this exemplary embodiment can be used for an array substrate.

In this way, with a storage method of this exemplary embodiment, it is possible to prevent substances that inhibit measurement, and suppress deterioration of property even in storage for a long time.

Industrial Applicability

The present invention relates to a sensor chip used for, for example, a biosensor or a chemical substance identification sensor for adsorbing a material substance on the surface thereof and measuring the substance, and a storage method of the sensor chip, which can prevent the sealing property from being deteriorated with the lapse of storage time.

Reference Marks In Drawings

101, 301a, 301b, 600, 2012, 3011, 3012 sensor chip
102 well
103 first electrolytic solution
104 second electrolytic solution
105 flow passage
106, 206, 306, 506 diaphragm
107 first electrode
108 second electrode
109, 209, 309, 309a, 309b through hole
110, 310, 510 first surface
111, 311, 511 second surface
112, 312a, 312b specimen
113 wall layer
114 concave portion
115a silicon layer
115b silicon dioxide layer
116 oxide film
117, 517 noncrystalline solid layer
500 sensor device
518 nanofiber

The invention claimed is:

1. A sensor chip for measuring a property of a substance by adsorbing the substance on a surface thereof, the sensor chip comprising:
   a diaphragm including a first surface, a second surface, and at least one through hole penetrating from the first surface to the second surface,
   wherein at least one of the first surface and the second surface has an adsorbing region of the substance, the adsorbing region and an inner wall surface of the through hole are covered with a noncrystalline solid layer including SiOX as a main component, in which substance X does not include oxygen and is an element having higher electronegativity than that of silicon, and
   an oxide film is formed between the noncrystalline solid layer and the first surface.

2. The sensor chip of claim 1, wherein a composition ratio in terms of a number of atoms of the substance X is exponentially reduced in a thickness direction of the diaphragm.

3. The sensor chip of claim 1, wherein the substance X is nitrogen.

4. The sensor chip of claim 1, wherein the noncrystalline solid layer is formed on the first surface.

5. The sensor chip of claim 1, wherein the noncrystalline solid layer is formed on both of the first surface and the second surface.

6. The sensor chip of claim 1, wherein a well for holding a solution including the substance is formed adjacent to the first surface.

7. The sensor chip of claim 1, wherein the second surface is provided at an opposite side to the first surface.

8. The sensor chip of claim 1, wherein the composition ratio in terms of the number of atoms in an outermost surface of substance X is not less than 3.6% and not more than 30%.

9. The sensor chip of claim 1, wherein the noncrystalline solid layer covers the through hole from the first surface to the second surface.

10. The sensor chip of claim 1, wherein the noncrystalline solid layer covers an entire surface of the sensor chip.

* * * * *